United States Patent
Du

(10) Patent No.: US 10,617,369 B2
(45) Date of Patent: Apr. 14, 2020

(54) ANTI-SCATTER GRID FOR RADIATION DETECTOR

(71) Applicant: SHANGHAI UNITED IMAGING HEALTHCARE CO., LTD., Shanghai (CN)

(72) Inventor: Yanfeng Du, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 161 days.

(21) Appl. No.: 15/308,369

(22) PCT Filed: Oct. 30, 2015

(86) PCT No.: PCT/CN2015/093477
§ 371 (c)(1),
(2) Date: Nov. 2, 2016

(87) PCT Pub. No.: WO2017/070961
PCT Pub. Date: May 4, 2017

(65) Prior Publication Data
US 2017/0265822 A1     Sep. 21, 2017

(51) Int. Cl.
*A61B 6/06*      (2006.01)
*A61B 6/03*      (2006.01)
(Continued)

(52) U.S. Cl.
CPC .................. *A61B 6/06* (2013.01); *A61B 6/03* (2013.01); *A61B 6/4216* (2013.01);
(Continued)

(58) Field of Classification Search
None
See application file for complete search history.

(56) References Cited

U.S. PATENT DOCUMENTS

2002/0037070 A1*   3/2002   Tang ..................... G21K 1/025
                                                           378/154
2004/0227092 A1*   11/2004   Ratzmann ............. G01T 1/1648
                                                            250/367
(Continued)

FOREIGN PATENT DOCUMENTS

WO       02065480 A1     8/2002

OTHER PUBLICATIONS

International Search Report for PCT/CN2015/093477 dated Jul. 21, 2016, 5 pages.
(Continued)

*Primary Examiner* — Hoon K Song
(74) *Attorney, Agent, or Firm* — Metis IP LLC

(57) ABSTRACT

An anti-scatter grid, a detector with such an anti-scatter grid and a radiation imaging system including such a detector with an anti-scatter grid are provided. The anti-scatter grid includes at least one grid wall. The parameters of the grid wall may be adjusted to arrive a uniform scatter-to-primary ratio. The parameters of the grid wall comprise thickness, height, shape, or position of the grid wall, or width of interspace between two grid walls. The detector includes the anti-scatter grid, at least one photosensor, and at least one scintillator. The radiation system includes a radiation generator, a radiation detector with the anti-scatter grid, and a processor.

19 Claims, 13 Drawing Sheets

(51) Int. Cl.
*A61B 6/00* (2006.01)
*G21K 1/02* (2006.01)

(52) U.S. Cl.
CPC .......... *A61B 6/4233* (2013.01); *A61B 6/4291* (2013.01); *G21K 1/025* (2013.01)

(56) References Cited

U.S. PATENT DOCUMENTS

| | | | |
|---|---|---|---|
| 2004/0251420 A1* | 12/2004 | Sun | G01T 1/2018 250/370.09 |
| 2009/0003530 A1 | 1/2009 | Van Vroonhoven | |
| 2009/0225938 A1 | 9/2009 | Zeitler et al. | |
| 2011/0019801 A1 | 1/2011 | Eichenseer et al. | |
| 2012/0087462 A1 | 4/2012 | Ikhlef | |
| 2016/0025870 A1* | 1/2016 | Bailey | A61B 6/032 378/19 |

OTHER PUBLICATIONS

The extended European search report in Europe Application No. 15896595.4 dated Jul. 18, 2018, 7 pages.

* cited by examiner

ANTI-SCATTER GRID FOR RADIATION DETECTOR

CROSS-REFERENCE TO RELATED APPLICATIONS

This present application is a U.S. national stage under 35 U.S.C. § 371 of International Application No. PCT/CN2015/093477, filed on Oct. 30, 2015, designating the United States of America, the contents of which are incorporated herein by reference.

TECHNICAL FIELD

The present disclosure generally relates to a radiation imaging system, and more particularly, to an anti-scatter grid for a detector and a radiation imaging system including such a detector.

BACKGROUND

A radiation imaging system (or "a radiography system") may be used in many fields such as medical diagnosis and therapy, industrial production and application, scientific experiment and research, national security, etc. Generally, radiation imaging is a technology that may allow non-invasive observation of the interior of a subject using radiation. As used herein, radiation may include a particle ray (for example, neutron, proton, electron, μ-meson, heavy ion, etc.), a photon ray (for example, X-ray, γ-ray, α-ray, β-ray, ultraviolet, laser, etc.), or the like, or any combination thereof. The information acquired by a radiation imaging system may include, e.g., structure, density, or lesions, etc., without damaging the subject. The term "subject" used herein may include a substance, a tissue, an organ, an object, a specimen, a body, or the like, or any combination thereof. Exemplary radiation imaging systems in the medical field may include an X-ray imaging system, for example, a Computerized Tomography (CT) system, a Digital Radiography (DR) system, or some multi-mode imaging system incorporating with a CT or DR system. Images with certain contrast may be generated by X-ray imaging based on the difference in absorptivity, reflectivity and transmissivity of different parts in the subject. The radiation passing through the subject in a straight line (termed as "primary radiation") may contribute to the generation of an image. Scatter radiation caused by the interaction between the radiation and the subject may interfere with the primary radiation. The scatter radiation may influence, for example, contrast-to-noise ratio (CNR) of a generated image. Thus, it is an enormous challenge to suppress or reduce the scatter radiation effectively and inexpensively in a radiation imaging system.

SUMMARY OF THE INVENTION

In an aspect of the present disclosure, an anti-scatter grid is provided. In some embodiments, the anti-scatter grid may include a plurality of grid walls, and the plurality of grid walls may be configured to arrive a uniform scatter-to-primary ratio.

In another aspect of the present disclosure, a detector is provided. In some embodiments, the detector may include at least one photosensor, at least one scintillator and at least one anti-scatter grid. In some embodiments, the anti-scatter grid may include a plurality of grid walls configured to provide a uniform scatter-to-primary ratio.

In still another aspect of the present disclosure, a radiation imaging system is provided. In some embodiments, the radiation imaging system may include a generator, a detector, and a processor. The generator may be configured to generate a radiation, the detector may be configured to detect the radiation, and the processor may be configured to process a radiation image. The detector may include at least one photosensor, at least one scintillator and at least one anti-scatter grid. In some embodiments, the anti-scatter grid may include a plurality of grid walls configured to provide a uniform scatter-to-primary ratio.

In some embodiments, the radiation system may further include a display device.

In some embodiments, a grid wall of the plurality of the grid walls may have parameters including thickness, height, shape, position of the grid wall, width of an interspace between two adjacent grid walls of the plurality of the grid walls, or the like, or any combination thereof.

In some embodiments, the detector may further include a substrate. In some embodiments, the substrate may be a chip.

In some embodiments, the substrate may be covered by the photosensor, and the photosensor may be covered by the scintillator, and the scintillator may be covered by the anti-scatter grid.

In some embodiments, the photosensor at a same substrate may have a same size and be arranged in a regular way.

In some embodiments, a scintillator may cover or correspond to a photosensor.

In some embodiments, the scintillator on a substrate may have the same size as its corresponding photosensor and align with its corresponding photosensor.

In some embodiments, the scintillator near an edge of the substrate may be no less than its corresponding photosensor and align to the left or right with its corresponding photosensor.

In some embodiments, a grid wall of the plurality of the grid walls may be located at a gap between two adjacent scintillators.

In some embodiments, the centerline of a grid wall of the plurality of the grid walls may be offset from the centerline of the gap between two adjacent scintillators.

In some embodiments, the thickness of grid wall of the plurality of the grid walls may be no less than the gap between two adjacent scintillators.

In some embodiments, the interspace between two adjacent grid walls of the plurality of the grid walls may be uniform.

In some embodiments, the uniform scatter-to-primary ratio may include a ratio of the width of the interspace between two adjacent grid walls of the plurality of grid walls to the height of the two adjacent grid walls of the plurality of grid walls. In some embodiments, the shape of the grid wall of the plurality of the grid walls in a longitudinal section may include a rectangle, a trapezoid, a T shape, or an irregular shape, or the like, or any combination.

In some embodiments, the grid wall of T shape may include a first part and a second part, wherein the first part may have a first thickness and a first height, and the second part may have a second thickness and a second height.

In some embodiments, the first thickness may be no less than the second thickness.

In some embodiments, the first height may be no more than the first height.

In some embodiments, the anti-scatter grid may be a parallel anti-scatter grid or a focused anti-scatter grid.

In some embodiments, the radiation used in the radiation system may be X-ray, γ-ray, α-ray, β-ray, ultraviolet, laser, neutron, proton, electron, μ-meson or heavy ion, or the like, or any combination thereof.

In some embodiments, the X-ray imaging system may be a Computed Tomography (CT) system, a Digital Radiography (DR) system, a Computed Tomography-Positron Emission Tomography (CT-PET) system, a Computed Tomography-Magnetic Resonance Imaging (CT-MRI) system, an X-ray security system or an X-ray foreign matter detection system, or the like, or any combination thereof.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the disclosed embodiments. Various modifications to the disclosed embodiments will be readily apparent to those skilled in the art, and the general principles defined herein may be applied to other embodiments and applications without departing from the spirits and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by other expression if they may achieve the same purpose.

It will be understood that when a unit, module or block is referred to as being "on," "connected to" or "coupled to" another unit, module, or block, it may be directly on, connected or coupled to the other unit, module, or block, or intervening unit, module, or block may be present, unless the context clearly indicates otherwise. As used herein, the term "and/or" includes any and all combinations of one or more of the associated listed items.

It will be understood that the term "regular" used herein is referred to as being "even," "uniform," or "identical," etc.

The terminology used herein is for the purposes of describing particular examples and embodiments only, and is not intended to be limiting. As used herein, the singular forms "a," "an" and "the" may be intended to include the plural forms as well, unless the context clearly indicates otherwise. It will be further understood that the terms "include," and/or "comprising," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

Figure 1:
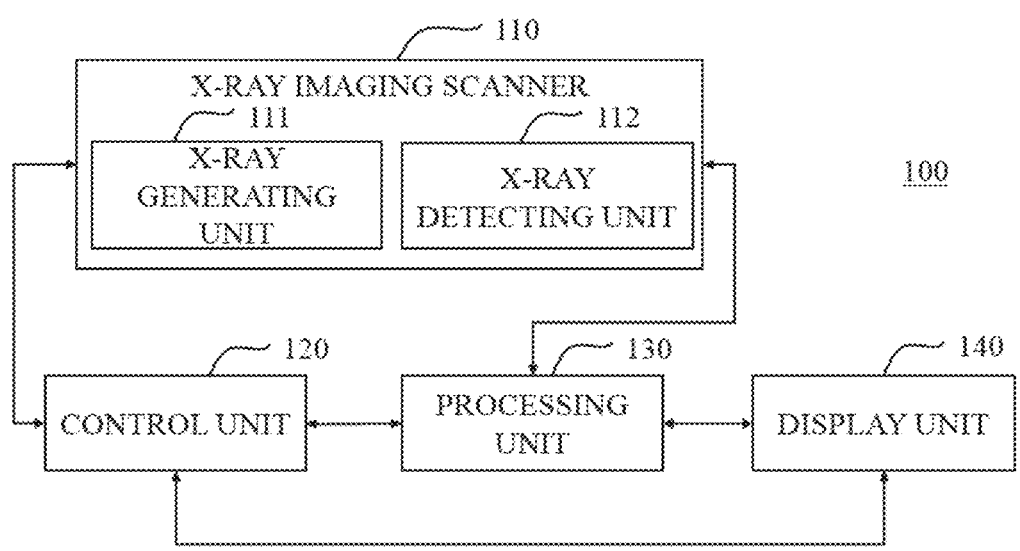
FIG. 1 is a block diagram depicting an X-ray imaging system according to some embodiments of the present disclosure.

FIG. 1 is a block diagram of an X-ray imaging system according to some embodiments of the present disclosure. It should be noted that X-ray imaging system described below is merely provided for illustrating an example of the radiation imaging system, and not intended to limit the scope of the present disclosure. The radiation used herein may include a particle ray, a photon ray, or the like, or any combination thereof. The particle ray may include neutron, proton, electron, meson, heavy ion, or the like, or any combination thereof. The photon beam may include X-ray, γ-ray, α-ray, β-ray, ultraviolet, laser, or the like, or any combination thereof. For better understanding the present disclosure, an X-ray imaging system is described as an example of a radiation imaging system. The X-ray imaging system may find its applications in different fields such as medicine or industry. In some embodiments of medical diagnosis, the X-ray imaging system may be a Computed Tomography (CT) system, a Digital Radiography (DR) system or may be used in some other multi-modality system, e.g., a Computed Tomography-Positron Emission Tomography (CT-PET) system, a Computed Tomography-Magnetic Resonance Imaging (CT-MRI) system. In some embodiments of industrial application, the system may be used in internal inspection of components e.g., flaw detection, security scanning, failure analysis, metrology, assembly analysis, void analysis, wall thickness analysis, or the like, or any combination thereof.

As illustrated in FIG. 1, an X-ray imaging system 100 may include, an X-ray imaging scanner 110, a control unit 120, a processing unit 130, and a display unit 140. The X-ray imaging scanner 110 may include an X-ray generating unit 111 and an X-ray detecting unit 112. In some embodiments, the control unit 120 may control the X-ray generating unit 111 and/or the X-ray detecting unit 112 of the X-ray imaging scanner 110, the processing unit 130, and/or the display unit

140. The processing unit 130 may process information received from the X-ray imaging scanner 110, the control unit 120, and/or the display unit 140 and generate one or more CT images based on the information and deliver the images to the display unit 140. The display unit 140 may be configured or used to receive input and/or display output information. The X-ray imaging scanner 110, the control unit 120, the processing unit 130 and the display unit 140 may be connected with each other directly, or with an intermediate unit (not shown in FIG. 1). The intermediate unit may be a visible component or an invisible field (radio, optical, sonic, electromagnetic induction, etc.). The connection between different units may be wired or wireless. The wired connection may include using a metal cable, an optical cable, a hybrid cable, an interface, or the like, or any combination thereof. The wireless connection may include using a Local Area Network (LAN), a Wide Area Network (WAN), a Bluetooth, a ZigBee, a Near Field Communication (NFC), or the like, or any combination thereof. It should be noted that the above description about the radiation system is merely an example. Obviously, to those skilled in the art, after understanding the basic principles of the connection between different units, the units and connection between the units may be modified or varied without departing from the principles. The modifications and variations are still within the scope of the present disclosure described above. In some embodiments, these units may be independent, and in some embodiments, part of the units may be integrated into one unit to work together.

The X-ray imaging scanner 110 may be configured or used to scan a subject (not shown in FIG. 1) under examination and generate the source data of an X-ray image. The subject may include a substance, a tissue, an organ, an object, a specimen, a body, or the like, or any combination thereof. In some embodiments, the subject may include a head, a breast, a lung, a pleura, a mediastinum, an abdomen, a long intestine, a small intestine, a bladder, a gallbladder, a triple warmer, a pelvic cavity, a backbone, extremities, a skeleton, a blood vessel, or the like, or any combination thereof. The X-ray generating unit 111 may be configured or used to generate X-rays to traverse the object under examination. The X-ray generating unit 111 may include an X-ray generator, a high-voltage tank, or other accessories. The X-ray generator may include one or more X-ray tubes which may emit X-rays by an X-ray tube. The X-ray generating unit 111 may be a cold cathode ion tube, a high vacuum hot cathode tube, a rotating anode tube, etc. The shape of the X-ray beam emitted may be a line, a narrow pencil, a narrow fan, a fan, a cone, a wedge, or the like, or an irregular shape, or any combination thereof. The X-ray tube in the X-ray generating unit 111 may be fixed at a point and it may translate or rotate in some scenarios.

The X-ray detecting unit 112 may be configured to receive the X-rays emitted from the X-ray generating unit 111 or other radiation source. The X-rays from the X-ray generating unit 111 may traverse the subject under examination. After receiving the X-rays, the X-ray detecting unit 112 may generate the source data of an X-ray image of the subject under examination. The term "source data" may be referred as the data that may be detected by the X-ray detecting unit 112, and the data may be transformed to the image data using an algorithm. As used herein, the term "image data" may be referred as the data that may be used to construct an image. The X-ray detecting unit 112 may be configured to receive X-rays and generate the source data of an X-ray image of the subject under examination. The X-ray detecting unit 112 may include an X-ray detector or other components. The shape of the X-ray detector may be flat, arc-shaped, circular, or the like, or any combination thereof. The fan angle of the arc-shaped detector may be an angle from 0° to 360°. The fan angle may be fixed or adjustable according to different conditions including, for example, the desired resolution of an image, the size of an image, the sensitivity of a detector, the stability of a detector, or the like, or any combination thereof. In some embodiments, the pixels of the detector may be the number of the smallest detecting units, e.g., the number of scintillator or photosensor etc. The pixels of the detector may be arranged in a single row, two rows or other number of rows. The X-ray detector may be one-dimensional, two-dimensional, or three-dimensional.

In some embodiments, there may be a collimator set between the X-ray generating unit 111 and a subject (termed as "pre-collimator"), or between the subject and the detecting unit 112 (termed as "post-collimator" or "anti-scatter grid"). The anti-scatter grid may be configured to absorb and/or block the scatter radiation from the subject under examination. As a result, the straight X-rays transmitted through the subject may be received by the X-ray detecting unit 112. It should be noted that the above description about the X-ray image unit is merely an example according to the present disclosure. Obviously, to those skilled in the art, after understanding the basic principles of the X-ray image unit, the form and details of the X-ray image unit may be modified or varied without departing from the principles. The modifications and variations are still within the scope of the present disclosure described above.

The control unit 120 may be configured to control the X-ray imaging scanner 110, the processing unit 130, the display unit 140, or other units or devices in the system according to some embodiments of the present disclosure. The control unit 120 may receive information from or send information to the X-ray imaging scanner 110, the processing 130, and/or the display unit 140. In some embodiments, the control unit 120 may provide certain voltage, and/or certain current to the X-ray imaging scanner 110 for scanning. The voltage and/or current may be different when different people with a specific value for age, weight, height, or so forth, is under examination. In some embodiments, the control unit 120 may receive some commands from the display unit 140 provided by, e.g., a user. Exemplary commands may include a scanning time, a location of the subject, or a rotating speed of the gantry, or the like, or any combination thereof. The control unit 120 may control the processing unit 130 to select different algorithms to process the source data of an X-ray image. The control unit 120 may transmit some commands to the display unit 140. Exemplary commands may include the size of an image, the location of an image, or the duration of an X-ray image to be displayed on a display screen. In some embodiments of the present disclosure, the X-ray image may be divided into several sub-portions for display, and the control unit 120 may control the number of the sub-portions. It should be noted that the above description about the control unit is merely an example according to the present disclosure. Obviously, to those skilled in the art, after understanding the basic principles of the control unit, the form and details of the control unit 120 may be modified or varied without departing from the principles. The modifications and variations are still within the scope of the present disclosure described above.

The processing unit 130 may be configured to process different kinds of information received from different units including the X-ray imaging scanner 110, the control unit 120, the display unit 140, or other units that may generate information. The processing unit 130 may process the data from the X-ray imaging scanner 110 to generate the X-ray image of an object under examination with different algorithms including a filtered back projection, an n-PI, or a tomosynthesis. The processing unit 130 may transfer the information from the display unit 140 to a particular form that can be identified by the control unit 120, and it may process the information from the control unit 120 to adjust the display unit 140. The information from the control unit 120 to control the X-ray imaging scanner 110 may be processed by the processing unit 130 firstly so that it can be identified. The above description of the processing unit 130 is merely for exemplary purposes, should not be understood as the only embodiments, and these examples do not limit the scope of the present disclosure. Obviously, to those skilled in the art, after understanding the basic principles of the processing unit, the form and details of the processing unit may be modified or varied without departing from the principles. The modifications and variations are still within the scope of the present disclosure described above.

The display unit 140 may be configured or used to receive input and/or display output information. The input and/or output information may include programs, software, algorithms, data, text, number, images, voice, or the like, or any combination thereof. For example, a user or an operator may input some initial parameters or conditions to initiate a scan. Said parameters or conditions may include the scanning time, the location of the object for scanning, or the rotating speed of the gantry. As another example, some information may be imported from external resource, such as a floppy disk, a hard disk, a wireless terminal, or the like, or any combination thereof. The display unit 140 may show the X-ray image of an object from the processing unit 130 to the user. The display unit 140 may receive the information from the control unit 120 to adjust some parameters for displaying. Said parameters may include, but are not limited to the size of an image, the location of an image, or the time duration of an image remains on a display screen. The display unit 140 may display the whole or part of an X-ray image. In some embodiments, an X-ray image may be divided into several portions, which may be display on a screen at the same time or in a certain order. And according to some embodiments of the present disclosure, the user or the operator may select one or more portions to display in some conditions. It should be noted that the above description about the display unit is merely an example according to the present disclosure. Obviously, to those skilled in the art, after understanding the basic principles of the display unit, the form and details of the display unit may be modified or varied without departing from the principles. The modifications and variations are still within the scope of the present disclosure described above.

It should be noted that the above description of the X-ray imaging system 100 is merely provided for the purposes of illustration, and not intended to limit the scope of the present disclosure. For persons having ordinary skills in the art, multiple variations and modifications may be made under the teachings of the present disclosure. For example, the assembly and/or function of the X-ray imaging system 100 may be varied or changed according to specific implementation scenarios. Merely by way of example, some other components may be added into the X-ray imaging system 100, such as a patient positioning unit, a high-voltage tank, an amplifier unit, a storage unit, an analog-to-digital converter, a digital-to-analog converter, an interface circuit, or the like, or any combination thereof. Note that the X-ray imaging system may be a traditional or a single-modality medical system, or a multi-modality system including, e.g., a Positron Emission Tomography-Computed Tomography (PET-CT) system, a Computed Tomography-Magnetic Resonance Imaging (CT-MRI) system, a remote medical X-ray imaging system, etc. However, those variations and modifications do not depart from the scope of the present disclosure.

Figure 2:
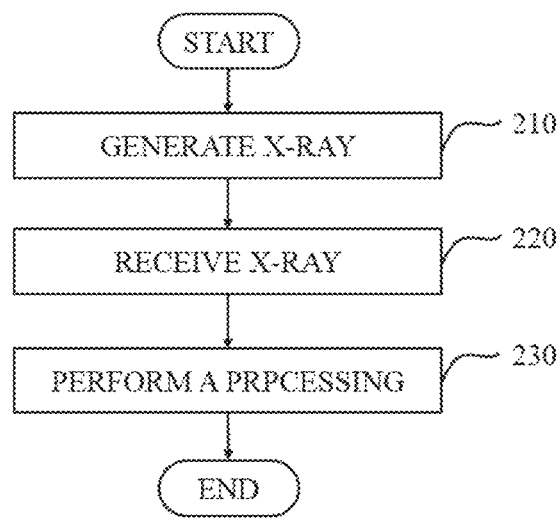
FIG. 2 is a flowchart illustrating a process for X-ray imaging according to some embodiments of the present disclosure.

FIG. 2 depicts a flowchart illustrating the process of an X-ray scanning according to some embodiments of the present disclosure. It should be noted that X-ray scanning process described below is merely provided for illustrating an example of the radiation imaging, and not intended to limit the scope of the present disclosure. The radiation used herein may include a particle ray, a photon ray, or the like, or any combination thereof. The particle ray may include neutron, proton, electron, µ-meson, heavy ion, or the like, or any combination thereof. The photon beam may include X-ray, γ-ray, α-ray, β-ray, ultraviolet, laser, or the like, or any combination thereof.

As illustrated in FIG. 2, in step 210, X-rays are generated. X-rays may be generated by the X-ray generating unit 111, or another radiation source. In some embodiments, one X-ray tube in the X-ray generating unit 111 may emit an X-ray beam in the shape of a line, a narrow pencil, a narrow fan, a fan, a cone, a wedge, or the like, or an irregular shape, or any combination thereof. The fan angle of the X-ray beam may be a certain value from 0° to 360°. In some embodiments, before step 210, there may be some parameters to be set by a user or an operator. Said parameters may include the parameters for the gantry, for the X-ray tube, for the X-ray detector, for the display devices, or other devices or units in the system. Merely by way of example, a user may set parameters including a certain voltage, and/or a certain current for people with a specific value for age, weight, height, or so forth. In some embodiments, the gantry may be adjusted to a certain rotating speed according to some parameters. In some embodiments, the beam shape and the angle of a fan beam may be selected according to some parameters. The types of the X-ray detector may be selectable based on some parameters. It should be noted that the above description about the parameters is merely provided for the purposes of illustration, and not intended to limit the scope of the present disclosure. For persons having ordinary skills in the art, multiple variations and modifications about the parameters that are set may be made under the teachings of the present disclosure.

In step 220, the X-rays emitted may be received by, for example, the X-ray detecting unit 112 of the X-ray scanning imaging scanner 110. In some embodiments, the X-rays may be projected on the X-ray detector of the X-ray detecting unit 112, the X-rays may include the X-rays traversing the subject under examination, the X-rays directly emitted from the X-ray generating unit 111, and/or the X-rays from other radiation sources. Parts of the X-rays may be blocked and/or absorbed by the anti-scatted grid set on the X-ray detector. In some embodiments, the X-rays may first be converted to light energy by scintillators, and then electrical signals may be produced therefrom by photodiodes. The electrical signals may be transmitted to the processing unit 130. The method of transmitting the signals may be wired or wireless. It should be noted that the above description about the signal conversion is merely provided for the purposes of illustration, and not intended to limit the scope of the present disclosure. For persons having ordinary skills in the art, multiple variations and modifications in the form and structure may be made under the teaching of the present disclosure. For example, the scintillators may be replaced by other components which may absorb the radiation and generate light energy, and the photodiodes may be replaced by other components which may be capable of converting the light energy to electrical signals.

The received signals are processed in step 230. In some embodiments, the processing unit 130 may process the data from the X-ray detector to generate the X-ray image data of a subject under examination with different algorithms including a filtered back projection, an n-PI, or a tomosynthesis. In this step, the image may be calibrated by using a calibration algorithm. In some embodiments, the image data, the calibrated data and/or the received signals by the processing unit 130 may be stored in some storage units or devices. A storage unit or device may store information by the way of electric, magnetic, or optical energy, etc. The device that store information by the way of electric energy may include RAM (Random Access Memory), ROM (Read Only Memory) and or the like, or any combination thereof. The device that store information by the way of magnetic energy may include a hard disk, a floppy disk, a magnetic tape, a magnetic core memory, a bubble memory, a USB flash drive, or the like, or any combination thereof. The device that store information by the way of optical energy may include CD (Compact Disk), VCD (Video Compact Disk), or the like, or any combination thereof. The method to store may include sequential storage, link storage, hash storage, index storage, or the like, or any combination thereof.

The image data or the calibrated image may be shown to the user or operator via the display unit 140. In some embodiments, the X-ray image of the subject may be printed. In some embodiments, the calibrated or uncalibrated image data of the subject may be transmitted to the doctor of the patient directly, such the doctor may make some decisions according to the data received.

It should be noted that the above description about the process of X-ray scanning is merely an example according to the present disclosure. Obviously, to those skilled in the art, after understanding the basic principles of the process of X-ray scanning, the form and details of the process may be modified or varied without departing from the principles. In some embodiments, other steps may added in the process. For example, the results of the processing may be displayed on some devices, and the intermediated data and/or the final data of the process may be stored in the process. The modifications and variations are still within the scope of the present disclosure described above.

A radiation detector may refer to a device for detecting any detectable radiation and provide an output according to the detected radiation. The radiation used herein may include a particle ray, a photon ray, or the like, or any combination thereof. The particle ray may include neutron, proton, electron, μ-meson, heavy ion, or the like, or any combination thereof. The photon beam may include X-ray, γ-ray, α-ray, β-ray, ultraviolet, laser, or the like, or any combination thereof. For better understanding the present disclosure, an X-ray detector may be described in detail as exemplary embodiments of a radiation imaging system.

An X-ray detector may be a device configured to detect properties of X-ray including, e.g., energy, time, spectrum, flux, spatial distribution of each X-ray, etc. Different energy ranges of X-ray may be detected by different kinds of X-ray detectors. The X-ray detector may include a solid detector and a gas detector according to two their states. The solid X-ray detector may include semiconductor photodiode with scintillator, semiconductor photodiode without scintillator, CCD (Charge Coupled Device) detector, CMOS (Complementary Metal-Oxide-Semiconductor Transistor) sensor, scintillation detectors, photodiode arranged with amplifier, or the like, or any combination thereof. The gas X-ray detector may include gas ionization detector, gas proportional detector, etc. Different kinds of X-ray detectors may be used for different applications according to different detectable characters, such as imaging, dose measurement, physical experiment, etc. The X-ray detector may find its applications in different fields including medicine or industry. In some embodiments, it may be used as a Computed Tomography (CT) detector, a Digital Radiography (DR) detector or may be used in some other multi-modality system, e.g., a Computed Tomography-Positron Emission Tomography (CT-PET) system, a Computed Tomography-Magnetic Resonance Imaging (CT-MRI) system. In some embodiments, the detector may be used in many areas of industry for internal inspection of components e.g., flaw detection, security scanning, failure analysis, metrology, assembly analysis, void analysis, wall thickness analysis, or the like, or any combination thereof.

Those skilled in the art should understand that the above embodiments are merely to describe the present disclosure. There may be many modifications and variations to the present disclosure without departing from the spirits of the present disclosure. For example, in some embodiments of the present disclosure, the X-ray detector is used in a CT system as a CT detector. But it should also be noted that the X-ray detector may be any types and used in any X-ray detecting systems as a detector. Similar modifications and variations are still within the scope of the present disclosure described above.

In some embodiments of the present disclosure, the X-ray detector may include a flat panel detector, an arc-shaped detector, or any other shaped detector. The X-ray detector may also be different states of motion including the types of translate-rotate, rotate-rotate, rotate-static, spiral, or the like, or any combination thereof. The X-ray detector with different detectable range may include a one-dimensional detector, a two-dimensional detector, a three-dimensional detector, etc. The X-ray detector may be one single one and also may be a plurality of detectors, such as X-ray detector array. The number of the column and row in the X-ray detector array may be varied according to the different demands, e.g., image resolution, the whole size of the detector and pixel, cost, or the like. The size of the X-ray detector may be varied according to demands such as image resolution, sensitivity, stability, or the like, or any combination thereof. The X-ray detector may be arranged regularly or irregularly.

Those skilled in the art should understand that the above embodiments are only utilized to describe the present disclosure. There may be many modifications and variations to the present disclosure without departing from the spirits of the present disclosure. For example, the X-ray detector may be combined variously, e.g., flat panel and array and two dimensional, also may be other kind of combinations. Similar modifications and variations are still within the scope of the present disclosure described above.

Figure 3:
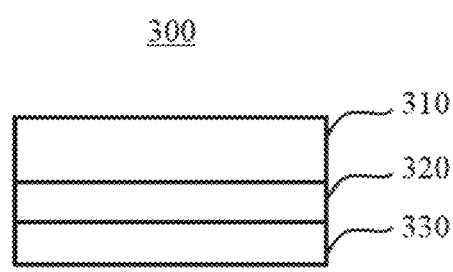
FIG. 3 is an illustration of a detector according to some embodiments of the present disclosure.

FIG. 3 is a diagram illustrating a structure of an X-ray detector 300 according to some embodiments of the present disclosure. The X-ray detector 300 may include a scintillator element 310, a photosensor element 320, a substrate element 330 and other components (not shown in FIG. 3). The scintillator element 310 may be configured to detect the X-rays, and it may be deposited on the photosensor element 320.

Those skilled in the art should understand that the above embodiments are only utilized to describe the present disclosure. There may be many modifications and variations to the present disclosure without departing from the spirits of the present disclosure. For example, the substrate element may be small chips to minimize the size of the X-ray detector. For another example, the X-ray detector may also be an assembly of scintillator elements, photovoltaic conversion elements, chips and other components. For still another example, the substrate or chip may be omitted in some embodiments. Similar modifications and variations are still within the scope of the present disclosure described above.

The substrate element 330 may be made from any material on which the photosensor element 320 may be mounted. In some embodiments, the material of substrate element 330 may be phenolic paper, epoxy paper, polyester glassy, epoxy glass, cotton, glass cloth, epoxy resin, polyols, polyester or the like materials, or any combination thereof, or composite of the above and other materials. The other materials here may be some reinforcement phase, e.g., fiber reinforcement, particle reinforcement, slice reinforcement or lamination reinforcement etc. For the fiber reinforced composites, the reinforcement phase may include fiber reinforced plastics, fiber reinforced rubber, fiber reinforced ceramic, fiber-reinforced metal, or the like, or any combination thereof. For the particle reinforcement, the reinforcement phase may include metal particles, ceramic particles and dispersion strengthening metal particles, etc., or any combination thereof. For the slice composite, the reinforcement phase may include graphite flake, talc, mica powder, micaceous iron oxide, glass flake, stainless steel flake, non-ferrous metal flake, non-ferrous metal oxide flakes, etc., or any combination thereof. For the lamination composite, the type may include double lamination, three-layer lamination and crisscross lamination, etc., or any combination thereof.

The scintillator element 310 may include materials that may absorb ionizing radiation and/or emit a fraction of the absorbed energy in the form of light. In some embodiments of the present discourse, the scintillator element 310 may absorb the X-rays and then emit visible or ultraviolet light photons. In some embodiments, the electron of X-ray passes through the scintillator element 310, it may lose energy and excites other electrons in the process; these excited electrons decay back to their ground state, giving off light as they do so. Similarly, the scintillator element 310 may produce a brief pulse of visible or ultraviolet photons corresponding to each X-ray photon that interacts with the scintillator material.

The types of scintillator element 310 in the present disclosure may include organic crystal scintillator, organic liquid scintillator, plastic scintillator, inorganic crystal scintillator, gaseous scintillator, glass scintillator, or the like, or any combination thereof. In some embodiments, the organic crystal scintillator may include anthracene ($C_{14}H_{10}$), stilbene ($C_{14}H_{12}$), naphthalene ($C_{10}H_8$), or the like, or any combination thereof. In some embodiments, the organic liquid scintillator may include a liquid solute and an organic solvent. The solute may include p-terphenyl ($C_{18}H_{14}$), PBD ($C_{20}H_{14}N_{20}$), butyl PBD ($C_{24}H_{22}N_{20}$), PPO ($C_{15}H_{11}NO$), POPOP ($C_{24}H_{16}N_{20}$), or the like, or any combination thereof. The solvent may include toluene, xylene, benzene, phenylcyclohexane, triethylbenzene, decalin, or the like, or any combination thereof. In some embodiments, the plastic scintillator may include a fluor, a base and a solid polymer matrix. The fluor may include polyphenyl hydrocarbons, oxazole, oxadiazoyl aryls, or the like, or any combination thereof. The base may include aromatic plastics, polymers with aromatic rings, polyvinyl xylene (PVX) polymethyl, 2,4-dimethyl, 2,4,5-trimethyl styrenes, polyvinyl diphenyl, polyvinyl naphthalene, polyvinyl tetrahydronaphthalene, copolymers, or the like, or any combination. In some embodiments, the inorganic crystal scintillator may include alkali metal halide, non-alkali crystal and/or other inorganic crystals. The alkali metal halide may include NaI (Tl), CsI (Tl), CsI (Na), CsI (pure), CsF, KI (Tl), LiI (Eu), or the like, or any combination thereof. The non-alkali crystal may include $BaF_2$, $CaF_2(Eu)$, $ZnS(Ag)$, $CaWO_4$, $CdWO_4$, YAG (Ce) ($Y_3Al_5O_{12}(Ce)$), GSO, LSO, or the like, or any combination thereof. In some embodiments, the gaseous scintillator may include different kinds of gas including nitrogen, helium, argon, krypton, xenon, or the like, or any combination thereof. In some embodiments, the glass scintillator may include cerium-activated lithium, boron silicates and/or any other glass materials. The thickness of the scintillator element 310 may be varied arbitrarily and not limited here. The size of the scintillator element 310 may be varied according to one or more conditions including, for example, image resolution, sensitivity, stability, the size of the detector or the like, or any combination thereof. Merely by way of example, the length and/or length of the scintillator may range from several micrometers to several hundreds of micrometers, e.g., 840 μm×740 μm. Merely by way of example, the height of the scintillator may range from several micrometers to several hundreds of micrometers, e.g., 500 μm. The shape of the scintillator element 310 may be circular, oval, rectangular, or the like, or any combination thereof. The scintillator element 310 may be arranged regularly, or irregularly on the photosensor element 320.

Those skilled in the art should understand that the above embodiments are only utilized to describe the present disclosure. There are many modifications and variations to the present disclosure without departing from the spirits of the present disclosure. For example, the type of the scintillator may be combined variously in order to achieve better detection effect. It should be noted that the scintillator may be in various states, such as crystal, powder, liquid or gas, or the like, or any combination thereof. Any scintillator which has a high detective efficiency, high conversion efficiency, low absorption, wide linear range and good processing performance, strong resistance to interference or the like may be used in the present disclosure. Variations, deformations and/or modifications like this are not departing from the spirits of the present disclosure.

The photosensor element 320 in the present disclosure may be a photoelectric conversion element which may firstly measure optical signals and then may converts the optical signals into electrical signals including, e.g., electrical currents, electrical voltages, and/or other electrical phenomena. The photosensor element 320 may process signals of light received from the scintillator element 310, and then convert to electrical signals. The photosensor element 320 in some embodiments of the present disclosure may include a phototube, a photomultiplier tube, a photodiode, an active-pixel sensor, a bolometer, a CCD, a gaseous ionization detector, a photoresistor, a phototransistor, or the like, or any combination thereof. The thickness of the photosensor element 320 may be varied arbitrarily but not limited here. The size of the photosensor element 320 may be varied one or more conditions including, for example, image resolution, sensitivity, stability, the size of the detector or the like, or any combination thereof. Merely by way of example, the length and/or length of the photosensor may range from several micrometers to several hundreds of micrometers, e.g., 840 μm×740 μm. Merely by way of example, the height of the photosensor may range from several micrometers to several hundreds of micrometers, e.g., 500 μm. The photosensor element 320 may be circular, oval, rectangular, or the like, or any combination thereof. The photosensor element 320 may be arranged regularly, or irregularly. For illustration purposes, a photodiode may be described in detail as exemplary embodiments of the photosensor element 320. The size of the photodiode may be different in different detection systems. The material of the photodiode may include silicon, germanium, indium gallium arsenide (InGaAs), lead sulfide, mercury cadmium telluride (HgCdTe), or the like, or any combination thereof. The type of the photodiode may include PN mode, PIN mode, avalanche mode, or the like, or the combination thereof. For illustration purposes, an avalanche photodiode may be described in detail as exemplary embodiments of the photodiode. In some embodiments, the avalanche photodiode also known as APD, which may include single-photon avalanche diode (SPAD), position sensitive avalanche photodiode (PSAPD), position sensitive photodiode, or the like, or any combination thereof. The model of the avalanche photodiode may include C30659-900-R5BH, C30659-900-R8AH, C30659-1060-R8BH, C30659-1060-3AH, C30659-1550-R08BH, C30659-1550-R2AH, C30919E, C30950EH, LLAM-1550-R2A, LLAM-1060-R8BH, HUV-1100BGH, HUV-2000BH, or the like, or any combination.

Those skilled in the art should understand that the above embodiments are only utilized to describe the present disclosure. There are many modifications, deformations and variations to the present disclosure without departing from the spirits of the present disclosure. For example, the photosensor element in the present disclosure may be any photosensor device which has a high sensitivity, high resolution, fast response, reliable performance or any other properties for a better image. It should be noted that the photosensors above are just an example for easy understanding, variations, deformations and/or modifications like this are not departing from the spirits of the present disclosure.

The substrate element 330 may be a solid substance providing a support for the X-ray detector 300. The substrate element 330 may be under the photosensor element 320. The size of the substrate element 330 may be varied according to the size of the detector. The substrate element 330 may be a thin slice or a thick one. The thickness of the substrate element 330 may be varied arbitrarily and not limited here. The overall shape of the substrate element 330 may be planar, arc-shaped, or any other shaped substrate in accordance to the different shapes of the X-ray detector 300. Each part of the substrate element 330 may be circular, oval, rectangular, or the like, or any combination thereof. The substrate element 330 may be arranged regularly, or irregularly. The materials of the substrate element 330 may include semiconducting materials or insulating materials. In some embodiments, the semiconducting materials may include elemental materials and compound materials. The elemental material may include silicon, germanium, carbon, tin, or the like, or any combination thereof. The compound material may include silicon dioxide, silicon nitride, silicon carbide, aluminum oxide, sapphire, germanium, gallium arsenide (GaAs), an alloy of silicon and germanium, indium phosphide (InP), poly (3-hexylthiophene), poly (p-phenylene vinylene), polyacetylene, or the like, or their derivatives, or any combination thereof. In some embodiments, the insulating materials may include glass, porcelain, paper, polymers, plastics, or the like, or any combination thereof.

Those skilled in the art should understand that the above embodiments are merely used to describe the present disclosure. There are many modifications, deformations and variations to the present disclosure without departing from the spirits of the present disclosure. For example, the substrate element in the present disclosure may also be a chip, a substrate, a printed circuit board (PCB), or any the like which may be connected with the photosensor to output electrical signals or a chip which process the data from the photosensor. It should be noted that the substrate illustrated above are just examples for easy understanding, variations, deformations and/or modifications like this are not departing from the sprits of the present disclosure.

In some embodiments, the other components in the present disclosure may include an anti-scatter device, a sensor, a control device, a filter, or the like, or any combination thereof. The anti-scatter device may include a grid, a plate, a collimator, or other device anti-scattering the X-ray, or any combination thereof. The sensor may be various sensors which may monitor the condition or environment of detecting, such as temperature sensor, humidity sensor, pressure sensor, gas sensor, ultrasonic sensor, or the like, or any other combination thereof. The control device may include devices which may alter the condition or environment of detecting.

Those skilled in the art should understand that the above embodiments are only utilized to describe the present disclosure. There are many modifications, deformations and variations to the present disclosure without departing from the spirits of the present disclosure. For example, an anti-scatter device and sensor may be added in order to attain high quality images. It should be noted that the filter, sensor, control device and anti-scatter and so on is not necessary for the X-ray detector. Variations, deformations and/or modifications like this are not departing from the sprits of the present disclosure.

In some embodiments, a radiation scattering phenomenon may exist in the radiation imaging system. As described elsewhere in the present disclosure, the radiation source may include photon ray and particle ray. The photon ray may include X-ray, γ-ray, α-ray, β-ray, ultraviolet, laser, or the like, or any combination thereof. The particle ray may include neutron, proton, electron, μ-meson, heavy ion, or the like, or any combination thereof. For illustration purposes, the following description is provided assuming exemplary embodiments of one kind of radiation source. It is understood that this is not intended to limit the scope the present disclosure to the exemplary embodiments of the radiation source.

Figure 4:
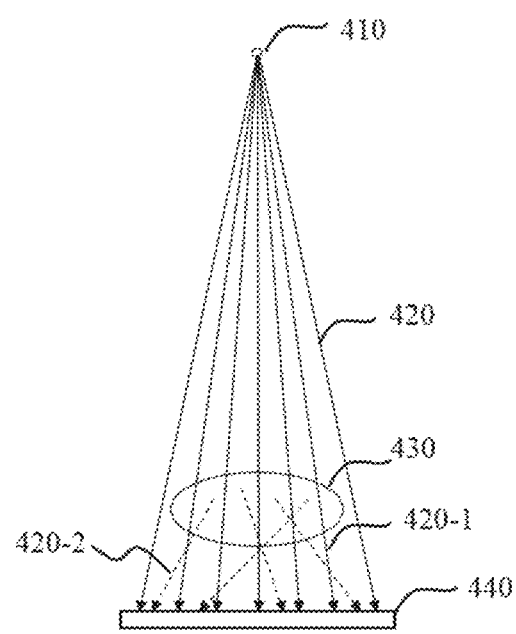
FIG. 4 is an illustration of an X-ray scatter phenomenon according to some embodiments of the present disclosure.

Merely by way of example, FIG. 4 is a diagram illustrating the X-ray scattering phenomenon in an X-ray imaging system according to some embodiments of the disclosure. As shown in this figure, one or more bundles of X-ray beam 420 (composed of X-rays) may generated from an X-ray generator 410. A subject 430 may be irradiated by the X-ray beam 420 during an imaging process. In some embodiments, the X-ray beam 420 may be absorbed by the subject 430 and the remainder X-ray 420-1 (termed as "primary radiation") of X-ray beam 420 may pass through the subject 430 directly and received by an X-ray detector 440. Different parts of the subject 430 may have different absorption properties of X-ray, thus a radiographic image with specific image contrast may be formed by detecting the difference of X-ray dose received. In some embodiments, the X-ray beam 420 may be influenced by the subject 430 and generate a scattered X-ray 420-2 (termed as "scatter radiation"). The scattered X-ray 420-2 may diverge from the original path of the X-ray beam 420 and arrive at any area at the X-ray detector 440 by random. The scattered X-ray 420-2 may cause cupping and streak artifacts, and/or degrade the image contrast-to-noise ratio (CNR). The subject 430 may endure much more radiation dose if an image with same contrast were to be obtained.

Note that the above diagram is purely for illustration, and that the present disclosure is not limited to this embodiment. The persons having ordinary skills in the art may make some variations, deformations and/or modifications without any creativity. For example, the X-ray beam may be replaced by γ-ray, neutron, proton, electron, μ-meson, heavy ion, or the like, or any combination thereof. The X-ray imaging system may be replaced by e.g., a CT imaging system, an impurity detecting system, a security checking system, etc. Variations, deformations and/or modifications like this are not departing from the spirits of the present disclosure.

Figure 5:
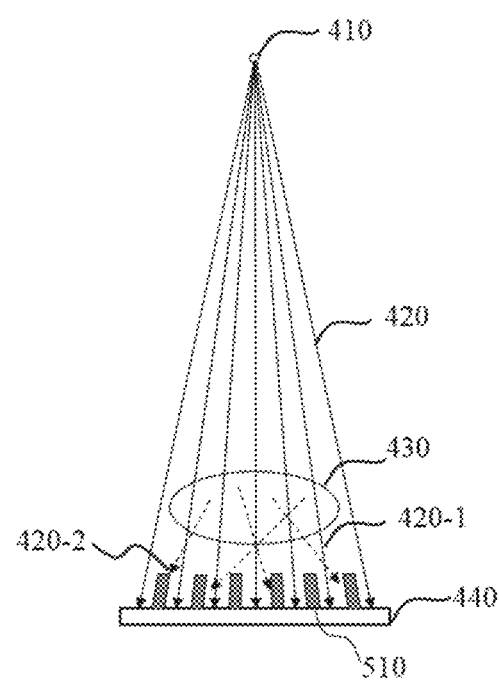
FIG. 5 illustrates a mechanism for suppressing X-ray scatter according to some embodiments of the present disclosure.

In some embodiments of the present disclosure, one or more mechanisms may be adopted to suppress the scatter radiation in an X-ray imaging system. The scatter suppressing methods may include a measurement-based method and/or a non-measurement-based method. In some embodiments of using the measurement-based method, a beam blocker may be applied to acquire scatter samples. The beam blocker applied in the measurement-based method may include a stationary beam blocker and a moving beam blocker. The non-measurement-based method may prevent scatter radiation from reaching the X-ray detector by using an anti-scatter module 510, which is located between the subject 430 and the X-ray detector 440, as shown in FIG. 5. The anti-scatter module 510 may be configured to absorb and limit the amount of the scatter radiation deviated from the X-ray beam 420. In some embodiments, the anti-scatter module 510 may include a collimator, an anti-scatter collimator, an anti-scatter plate, an anti-scatter septa, an anti-scatter grid, or the like, or any combination thereof. For convenience of illustration, the anti-scatter grid would be described below in detail as an example to understand the present disclosure without limiting its scope.

Figure 6:
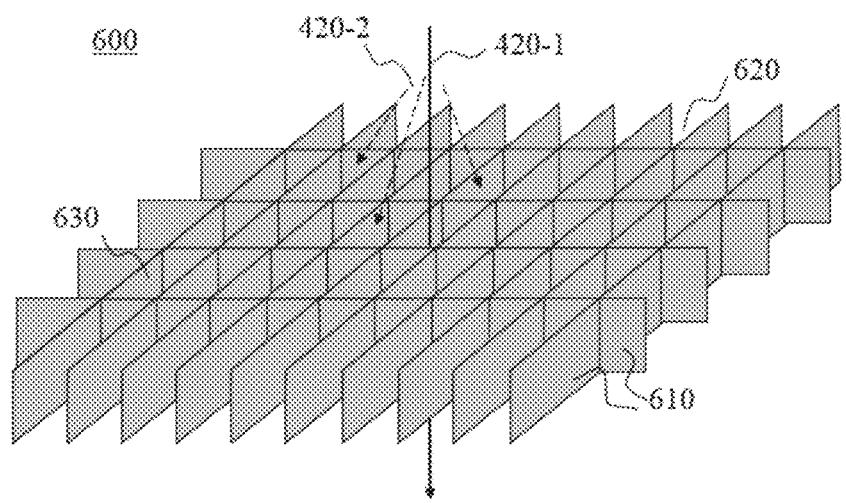
FIG. 6 illustrates an anti-scatter grid according to some embodiments of the present disclosure.

FIG. 6 is a diagram illustrating an anti-scatter grid according to some embodiments of the present disclosure. As shown in the figure, the anti-scatter grid 600 may include a strip of absorbing medium 610 and an interspace transparent medium 620. The absorbing medium 610 may absorb the scatter radiation 420-2 and minimize attenuation of the primary radiation 420-1. The transparent medium 620 may give a passage of the primary radiation 420-1. The absorbing medium 610 and the transparent medium 620 may be comprised by materials with different absorptivity. For example, the absorptivity of the absorbing medium 610 may be bigger than the transparent medium 620's. In some embodiments, the absorbing medium 610 may be formed with highly absorbing materials whose density is great or whose atoms is with heavy nuclei. Merely by way of example, the absorbing materials may include lead, gold, tungsten, depleted uranium, thorium, barium sulfate, tantalum, iridium, osmium, or the like, or any combination thereof. The transparent medium 620 may include any material whose absorbability is smaller than the absorbing medium 610. The transparent material may include metal, an alloy thereof, an inorganic material, an organic material, or the like, or any combination thereof. Exemplary metal include aluminum, magnesium, titanium, or the like, or any combination thereof. Exemplary inorganic material may include a carbon fiber, glass, etc. Exemplary organic material may include plastic, rubber, etc. Note that the above embodiments are purely provided for illustration, the present disclosure is not limited to these embodiments. Persons having ordinary skills in the art may make some variations, deformations and/or modifications without any creativity according to the present disclosure. In some embodiments, some materials with other properties may be added in the anti-scatter grid 600. In some embodiments, the anti-scatter grid 600 may also be incorporated with some components such as electrodes. Variations, deformations and/or modifications like this are not departing from the spirits of the present disclosure.

In some embodiments, the absorbing medium 610 of an anti-scatter grid 600 may include one or more walls, strips, plates, laminations or other components. For illustration purposes, term "wall" may be used to describe some embodiments according to the present disclosure. The walls may be connected with the transparent medium 620 in an alternating manner and thus an anti-scatter grid 600 may be assembled. In some embodiments, the connecting methods of the absorbing medium and the transparent medium may include physical type and/or chemical type. The physical type include using mechanical principles. The chemical type include using an adhesive material. The anti-scatter grid 600 may include parallel grid and/or focused grid. In some embodiments, the absorbing medium 610 may have a linear geometry in one direction, for example, the walls may be parallel with each other, as shown in FIG. 6. In some other embodiments, the absorbing medium 610 may be cross-hatched in two direction, for example, the walls may be crosswise with each other with an angle from 0° to 90°. The structure of the grid may include a parallel type and a focused type. In the plane parallel to the X-ray beam, the walls of the parallel grid may be arranged in parallel with each other, and the walls of the focused grid may be set by a slight angle to each other to make all the strips focus to the X-ray source. The framework of the anti-scatter grid 600 may be non-detachable type or detachable type. In some embodiments of non-detachable framework, the anti-scatter grid 600 may be generated by some materials processing technologies including cutting, casting, welding, lithographic micromachining, stacking, 3D printing, or the like, or any combination thereof. In some embodiments of the detachable framework, the anti-scatter grid 600 may be assembled in some detachable manner include, e.g., plugging, riveting, screwing, interlocking, or the like, or any combination thereof.

For illustration purposes, the interspace between the peripheral walls may be defined as a "grid cell" in the anti-scatter grid 600. In a cross-section, the shape of the grid cell 630 may be a triangle, a rectangle, a square, a trapezoid, a pentagon, a hexagon, a circular, an ovoid, an ellipse, an irregular shape, or the like, or any combination thereof. For example, the cross-section of the grid cell 630 may be uniform horizontally and vertically, which means that all the grid cells 630 may have the same shape and that the distance (termed as "center distance") between two adjacent grid cells are equal as well. In some embodiments, the grid cells 630 may be uniform in one direction and non-uniform in another direction. For example, the grid cells 630 may have a same shape and be separated by a same distance horizontally, while the grid cells 630 in vertical direction may illustrate a different pattern. In some embodiments, there may be merely one or more parts of the grid cells 630 following a different rule from the remainder. In some embodiments, the variances of shape and/or center distance of the grid cells may be by random, by step and step, or by other manner. In the longitudinal section parallel to the X-ray beam, the shape of the grid wall may be a triangle, a rectangle, a square, a trapezoid, a sector, an irregular shape, or the like, or any combination thereof. Merely by way of example, in the embodiments of rectangle-shaped strip, its length, width, length-to-width ratio may be selected according to specific implementation scenarios. For example, the length may range from 10 to 30 mm, the width may be determined by some imaging demands. In some embodiments, the imaging demands may include a processing technology, pixels of an image, contrast of an image, a radiation dose of a pixel, or the like, or any combination thereof.

It should be noted that the above description of the anti-scatter grid 600 is merely provided for the purposes of illustration, and not intended to limit the scope of the present disclosure. For persons having ordinary skills in the art, multiple variations and modifications may be made under the teachings of the present disclosure. In some embodiments, assembly method, size, shape and/or amount of the grid cell 630 may be varied or changed according to specific implementation scenarios. Merely by way of example, the cross-section shape of the grid cell may be a hollow circular, and the transparent medium 620 may be in the center of the grid cell 630. However, those variations and modifications do not depart from the scope of the present disclosure.

The anti-scatter grid 600 may be posited between a subject and a detector, as described elsewhere in the present disclosure, a detector may include a scintillator, a photosensor, and/or a substrate. The substrate may be some devices which may support the photosensor and/or execute the data converting. In some embodiments, the substrate may be a chip. For illustration purposes, a detector with a chip as a substrate may be described in detail as exemplary embodiments of a detector. In this scenario, the chip may be incorporated with a photosensor. The number of the chips in a detector may be one or more, it may depend on the imaging region or other factors. In some embodiments of multiple-chips-on-a-detector assembly, there may be a gap between two adjacent chips. This may be due to several factors including, e.g., an additional protecting region in the edge of the chip, a gap between two chips, etc. In some embodiments, the number of the photosensors on one chip may be determined by considerations including, for example, a desired image quality, a manufacturing technology, or the like, or any combination thereof. Factors of an image quality may include an image size, an image resolution, an image contrast, a contrast-to-noise ratio (CNR), or the like, or any combination thereof. Factors of a manufacturing technology may include a machining error, an alignment error, etc. Merely by way of example, the array of the photosensors may be 4×4, 3×5, or any other array.

In the embodiments of multiple-photosensors-on-a-chip assembly, the gaps of two adjacent photosensors in the same chip may be different from the gaps of two adjacent photosensors from two neighboring chips. This may be due to several factors including, e.g., an additional protecting region in the edge of the chip, a gap between two chips, etc. In some embodiments, the number of the scintillators on the photosensors may be the same as or different from the number of the photosensors. In some embodiments, the number of scintillators and the number of photosensors may be identical. The scintillators and the photosensors may align with each other. A scintillator may correspond to a photosensor. A scintillator may overlap with a photosensor. Merely by way of example, a scintillator may be located above a photosensor. In the embodiments of the above mentioned alignment methods, the scintillator and the photosensor may be arranged evenly or unevenly, respectively. An anti-scatter grid may be arranged or set in the manner that a grid wall is located above the gap between two adjacent scintillators. The height, width, and/or height-to-width ratio may be determined by the demands of a primary radiation intensity, a scatter radiation intensity, a scatter-to-primary ratio (SPR), a making technology, or the like, or any combination thereof.

In some embodiments, shape of the substrate may be circular, oval, rectangular, rhombus, or the like, or any irregular shape, or any combination thereof. In the embodiments of more than one substrates, the substrates may be arranged regularly or irregularly. The number of the column and row of the substrates may be varied arbitrarily and not limited here.

In some embodiments, the photosensor element may be circular, oval, rectangular, rhombus, or the like, or any irregular shape, or any combination thereof. The photosensor element may be arranged regularly, or irregularly on the chip array. The number of the column and row of the photosensor array may be varied arbitrarily but not limited here. In some embodiments, the scintillator element may be circular, oval, rectangular, rhombus, or the like, or any irregular shape, or any combination thereof. The scintillator element may be arranged regularly or irregularly. The number of the column and row of the scintillator array may be varied arbitrarily but not limited here. In some embodiments, the top view of the anti-scatter grid 710 may be circular, oval, rectangular, rhombus, or the like, or any irregular shape, or any combination thereof. The longitudinal section view of the anti-scatter grid wall may be rectangular, trapezoid, triangle, or the like, or any irregular shape, or any combination thereof. The anti-scatter grid wall in one dimension may be parallel to each other, have an angle between each other, or may be focused to a focal point.

The connection between the anti-scatter grid and the X-ray detector, or the scintillator layer and the photosensor, or the photosensor and the substrate may be detachable or non-detachable, or the combination thereof. The detachable manner may be ways including a magnetic connection, a threaded connection, a pin connection, a hinged connection, a plugging connection, an interlocking connection, or the like, or any combination thereof. The non-detachable manner may be the way by of welding, riveting, casting, gluing, or the like, or any combination thereof.

For illustration purposes, the following description may be provided assuming the exemplary embodiments of the structure of a detector. It is understood that this is not intended to limit the scope the present disclosure to the exemplary embodiments of the detector.

Figure 7:
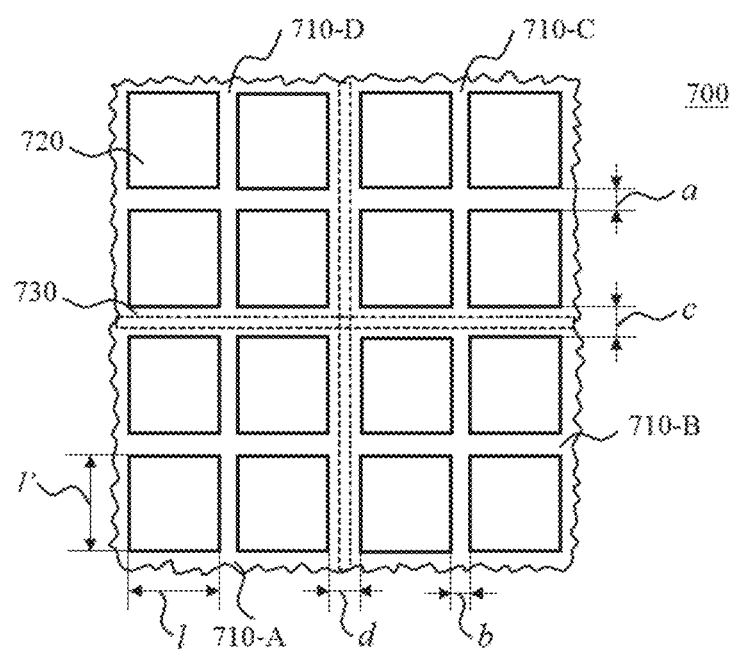
FIG. 7 illustrates a detector according to some embodiments of the present disclosure.

FIG. 7 is a diagram illustrating a part of a detector 700 in the top view according to some embodiments of the present disclosure. As illustrated in the figure, in a part of a detector 700, there may be four chips, i.e., 710-A, 710-B, 710-C and 710-D. Two of the four chips may be located side by side. The four chips may meet at a point. In some embodiments, the detector 700 may have different amounts of chips. The chip array may be one dimension and/or two dimension. In the embodiments of the one dimensional chip array, there may be some chips assembling in a line. For example, the array may be 1×1, 1×2, or any other array. In the embodiments of the two dimensional chip array, there may be more than one chips in both horizontal and vertical direction. For example, the array may be 2×2, 3×3, 2×3, or any other array. For illustration purposes, four adjacent chips chosen from one part of the detector 700 may be described in detail below. On each chip 710, there may be at least one photosensor 720. As illustrated elsewhere in the present disclosure, the number of the photosensors on one chip may be determined by the demands of an image quality and/or the demands of a making technology. For better understanding, there are at least four photosensors 720 one chip 710 in FIG. 7. The photosensors 720 may be arranged evenly or unevenly. In the embodiments of the even arrangement, the photosensors 720 may have a same length/and a same width l'. The length/and width l' may be the same or different. The gap a between two photosensors in vertical direction and the gap b between two photosensors in the horizontal direction may be identical everywhere in the detector shown in FIG. 7, respectively. In the embodiments of the uneven arrangement, the length/and width l' of each photosensor 720 may be different from another photosensor 720. The gap a between two photosensors in vertical direction and the gap b between two photosensors in the horizontal direction may not be identical everywhere, respectively. In some embodiments, there may be an additional protecting region (not shown in FIG. 7) near the edges of the chip 710, and/or a gap 730 between two adjacent chips. These may cause the gap c and the gap d between two photosensors in the edges of two neighbor chips be bigger than the gap a and the gap b, respectively. It should be noted that the above description of the detector 700 is merely provided for the purposes of illustration, and not intended to limit the scope of the present disclosure. For persons having ordinary skills in the art, multiple variations and modifications may be made under the teachings of the present disclosure. For example, the assembly, sizes and/or amount of the photosensor 720 may be varied or changed according to specific implementation scenarios. Merely by way of example, the sizes of photosensors 720 near the edge of the chip in the horizontal direction may be reduced to l" so that the sum of two photosensors on neighbor chips (i.e., l"+d+l") may be equal to the sum of two photosensors on one chip (i.e., l+d+l). The sizes of photosensors 720 near the edge of the chip in the horizontal direction may be reduced to l''' so that the sum of two photosensors on neighbor chips (i.e., l'''+c+l''') may be equal to the sum of two photosensors on one chip (i.e., l'+c+l'). However, those variations and modifications do not depart from the scope of the present disclosure.

Figure 8:
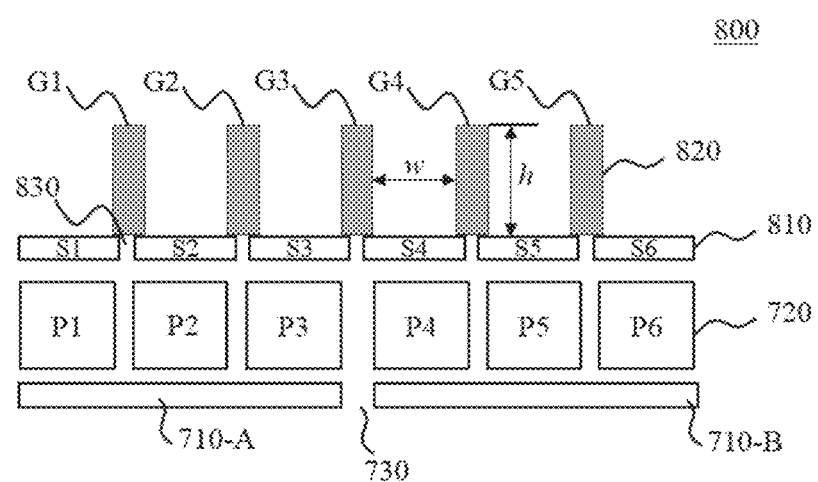
FIGS. 8-11 illustrate exemplary detectors with exemplary anti-scatter grids according to some embodiments of the present disclosure.

FIG. 8 is a diagram illustrating a longitudinal section of a part of a detector 800 in the front view of FIG. 7 according to some embodiments of the present disclosure. As shown in the figure, a scintillator 810 and an anti-scatter grid 820 may be located on the photosensor 720. For illustration purposes, the photosensor 720 may have the same size, structure, materials, amount, or other characteristics with the photosensor 720 shown in FIG. 8. It should be understood that this is not intended to limit the scope the present disclosure to the exemplary embodiments of the detector. In FIG. 8, the photosensor 720 may include photosensor P1, P2, P3, P4, P5 and P6. P1, P2 and P3 may be on a chip 710-A, and P4, P5 and P6 may be on another chip 710-B. In some embodiments, the photosensors on one chip may be arranged evenly and the gaps 740 between them may be identical as shown in FIG. 6. The photosensor P3 and photosensor P4 are near the edge of the chips, and their gap may be much bigger because there may be an additional protecting region and/or a gap 730 between two neighbor chips. The scintillator 810, i.e., scintillator S1 to S6 are assembled above the photosensor 720. The number of the scintillators 810 on the photosensors 720 may be the same with or different from the number of the photosensors 720. For illustration purposes, the exemplary embodiments of identical scintillator and photosensor amount may be described in detail below. In these embodiments, the scintillator 810 and the photosensor 720 may align with each other or in an overlapping manner. In some embodiments, the scintillator S1 and the photosensor P1 may have the same size. In some embodiments, the scintillator S1 and the photosensor P1 may align almost or exactly with each other (e.g., at one or more edges of the scintillator S1 and the corresponding one or more edges of the photosensor P1), so do the S2-P2, S3-P3, S4-P4, S5-P5 and S6-P6 pairs. In some embodiments of the overlapping structure, the scintillator S1 and the photosensor P1 may have different sizes and at least one edge may not be aligned. For illustration purposes, a structure in an overlapping alignment manner may be described. As shown in FIG. 8, the scintillator 810 may have the same size and be arranged evenly on the photosensors 720. As used herein, an even arrangement may indicate that the gaps between pairs of adjacent scintillators on a substrate may be identical. For instance, the gaps 830 between each two adjacent scintillators may be identical. As shown in the FIG. 8, the centerline of a gap 830 between two adjacent scintillators 810 may be offset from the centerline of the gap between two adjacent photosensors 720.

In some embodiments according to the present disclosure, an anti-scatter grid 820 may be placed on the scintillator 810. The anti-scatter grid 820 may include grid walls G1, G2, G3, G4 and G5. The structure, size, shape and/or materials may be as the description elsewhere in the present disclosure. The grid walls G1 to G5 of the anti-scatter grid 820 may be arranged in the manner of each grid wall on each gap. For example, the grid wall G1 may be placed above the gap 830 between the scintillator S1 and S2. The centerline of the grid wall G1 and the centerline of the gap of the scintillator S1 and S2 may coincide on a line, or have an offset distance. In some embodiments, the height, width, and/or height-to-thickness ratio of the grid walls may be determined by the demands of primary radiation intensity, scatter radiation intensity and/or scatter-to-primary ratio (SPR), as described elsewhere in the present disclosure.

It should be noted that the above description of the detector 800 is merely provided for the purposes of illustration, and not intended to limit the scope of the present disclosure. For persons having ordinary skills in the art, multiple variations and modifications may be made under the teachings of the present disclosure. For example, the assembly, sizes and/or amount of the scintillator 810 may be varied or changed according to specific implementation scenarios. Merely by way of example, the sizes of scintillators S3 and S4 near the edge of the chip in the horizontal direction may be added and the size of scintillators S1, S2, S5 and S6 are equal to that of the photosensor 720. However, those variations and modifications do not depart from the scope of the present disclosure.

Figure 9:
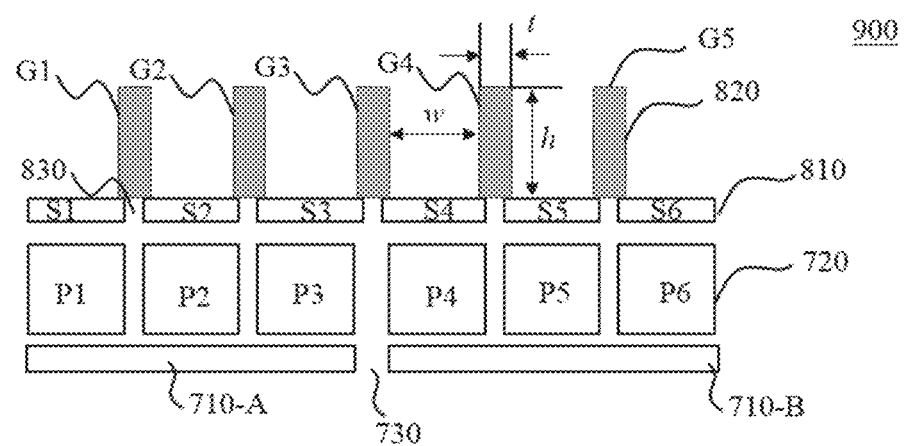

FIG. 9 shows a longitudinal section of a detector with an anti-scatter grid placed on it according to some embodiments of the present disclosure. As illustrated in the figure, the detector 900 may include a scintillator 810, a photosensor 720 and a chip 710. The scintillator 810 may be placed on the photosensor 720. The scintillator 810 may include scintillator S1, S2, S3, S4, S5 and S6. The photosensor 720 may include photosensor P1, P2, P3, P4, P5 and P6. In some embodiments, the scintillator S1 and photosensor P1 may have the same size and align almost or exactly with each other to the left and right edge, so do the S2-P2, S5-P5 and S6-P6 pairs. In some embodiments, the scintillators S3 and S4 near the chips 710-A and 710-B may have a bigger size than scintillator S1, S2, S5, or S6. The scintillator S3 and photosensor P3 may have different sizes and at least one edge may not be aligned, so does S4-P4 pair. The gaps 830 of each two adjacent scintillators may be identical, as shown in the FIG. 9. The centerline of gaps 830 between each two adjacent scintillators 810 may be in accordance with the centerline of gaps between each two adjacent photosensors 720. The anti-scatter grid 820 may include grid wall G1, G2, G3, G4 and G5. The grid wall G1 to G5 of the anti-scatter grid 820 with the thickness t and the height h may be mounted on the gaps between two adjacent scintillators. It should be noted that the number, shape, size or structure of the photosensor 720, the scintillator 810 and the anti-scatter grid 820 here are merely for the purposes of describing conveniently, and is not intended to be limiting. For persons having ordinary skills in the art, the number of the scintillator elements can be varied arbitrarily according to some embodiments of the present disclosure.

In some embodiments, there may be an additional protecting region (not shown in FIG. 9) near the edges of the chips 710-A and 710-B, and/or a gap 730 between two adjacent chips. These may cause that the gaps between two photosensors in the edges of two neighbor chips may be bigger than other gaps, i.e., the gap between photosensors P1 and P2 may be smaller than the gap between photosensors P3 and P4. The grid walls G1 to G5 of the anti-scatter grid 820 may be arranged in a manner of each-grid-wall-on-each-gap. For example, the grid wall G1 may be placed above the gap 830 between the scintillator S1 and S2 as shown in FIG. 7. The centerline of the grid wall G1 and the centerline of the gap of the scintillator S1 and S2 may coincide on a line, or have an offset distance. The thickness t and the height h of the grid walls G1 to G5 may be the same or different. The width w of primary radiation region between each two adjacent grid walls may be the same or different. In some embodiments, the thickness t and the height h of the grid walls and the width w of primary radiation region may be set according to some rules. For illustration purposes, the rule may be the scatter-to-primary ratio (SPR). In some embodiments, the SPR value may be calculated using the equation SPR=S/P, wherein P is the intensity of the primary radiation and S is the intensity of the scatter radiation.

It should be noted that the description of the structures of the detector and the anti-scatter grid is merely an example according to the present disclosure. Obviously, to those skilled in the art, after understanding the basic principles of the structures of the detector and the anti-scatter grid, the form and details of the structures of the detector and the anti-scatter grid may be modified or varied without departing from the principles. The modifications and variations are still within the scope of the present disclosure described above.

For example, in some embodiments, the length of each photosensor element may be the same or different, and the gaps between the photosensor elements may be the same or different. The length of each scintillator may be the same or different, and the gaps between two adjacent scintillators may be the same or different. In some embodiments of the present disclosure, the width w of the primary radiation region between the grid walls may be different or the same, the thickness t of the grid walls may be the same or different, and the thickness of the grid walls may be varied arbitrarily, the height h of the grid walls may be the same of different, and the height of the grid walls may be varied arbitrarily. In some embodiments, the grid walls of the anti-scatter grid 820 may be mounted on the gaps between the scintillator elements. In some embodiments, the grid walls of the anti-scatter grid 820 may be mounted totally on one scintillator. In some embodiments, the thickness t of the grid walls maybe equal to the width of the gaps between two adjacent scintillators. In some embodiments, the thickness t of the grid walls may be larger or smaller than the width of the gaps between two adjacent scintillators. In some embodiments, the vertical centerline of the walls may be on the same line with that of the gaps between two adjacent scintillators. In some embodiments, the vertical centerline of the grid walls may be on the left or right of that of the gaps between the scintillator elements.

In some embodiments, the space between the grid walls of the anti-scatter grid may be occupied by some transparent medium. The transparent medium may include, for example, gas, light metal, inorganic materials, or organic materials with low absorbing property of X-ray. For example, the gas may include oxygen, nitrogen, carbon dioxide, hydrogen, air, or the like, or any combination thereof. Exemplary metal may include aluminum, magnesium, titanium, or the like, or any combination thereof. Exemplary inorganic material may include a carbon fiber, glass, etc. Exemplary organic material may include plastic, rubber, etc. In some embodiments, the gaps between the scintillator elements and the gaps between the photosensor elements may be filled to absorbed/block the X-rays. The absorbing medium may be formed by highly absorbing materials, e.g., lead, gold, tungsten, depleted uranium, thorium, barium sulfate, tantalum, iridium, osmium, or the like, or any combination thereof. In some embodiments, the gaps between two photosensors or between two scintillators may be filled with some materials. The materials in the gaps may be the same as or be different from that in the gaps between the photosensor elements.

In some embodiments, each thickness t, height h and the position of each grid wall of the anti-scatter grid 820 may be determined by some parameters. In some embodiments, the parameters may include the uniformity of primary radiation received by each pixel of the scintillator, and/or the uniformity of scatter radiation absorbed by each grid wall (or the uniformity of scatter radiation absorbed by each pixel of the scintillator), and/or the uniformity of the scatter-to-primary ratio (SPR), and/or other parameters. The parameters described above may be realized by making the widths w of the primary region between the grid walls be the same, and/or the ratio of height h of the grid walls to the width w of the primary radiation region be the same, and/or the ratio of thickness t of the grid walls to the width w of the primary radiation region be the same. In some embodiments, the one dimensional physical quantities may be replaced by a two dimensional quantities. For example, the thickness t of a grid wall may be replaced by a cross-section area of the grid wall, and the width w of a primary radiation region may be replaced by a cross-section area of a primary radiation region. In these embodiments, the principle to determine the thickness or position of a grid wall in one dimension may be applicable as well in determining the area or position of a grid wall in two dimension.

In some embodiments, the parameters to determine the thickness t, the height h and the position of the grid walls may also include the effective utilization rate of the pixels of the scintillators, the error of the size of the scintillators, the error existing in making the anti-scatter grid, the error lying in aligning the anti-scatter grid with the X-ray detector, or the like, or any combination thereof. For illustration purposes, exemplary embodiments of improving the effective utilization rate of the pixels of the scintillators may be described below. For example, the thickness t of the grid walls may be as thin as possible so that more primary radiation may be received by the scintillators, and at the same time, the thickness t of the grid walls may be large enough so that the edges of each scintillator element may not be exposed.

It should be noted that the above description of the detector 900 is merely provided for the purposes of illustration, and not intended to limit the scope of the present disclosure. For persons having ordinary skills in the art, multiple variations and modifications may be made under the teachings of the present disclosure. In some embodiments, assembly method, size, shape, array type and/or amount of the photosensors, the scintillators, the anti-scatter grids may be varied or changed according to specific implementation scenarios. Merely by way of example, the amount of the anti-scatter grids placed on the detector may be one or more. And the array of the anti-scatter grids on the detector may even or uneven. However, those variations and modifications do not depart from the scope of the present disclosure.

Figure 10:
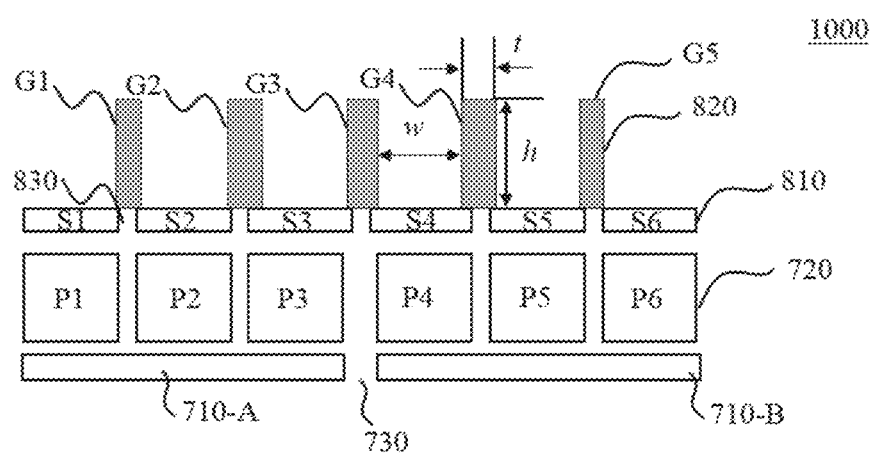

FIG. 10 illustrates a longitudinal section of an X-ray detector with an anti-scatter placed on it according to some embodiments in the present disclosure. As illustrated in the figure, the detector 1000 may include a scintillator 810, a photosensor 720 and a chip 710. The scintillator 810 may be placed on the photosensor 720. The scintillator 810 may include scintillators S1, S2, S3, S4, S5, and S6. The photosensor 720 may include photosensors P1, P2, P3, P4, P5 and P6. In some embodiments, the scintillator S1 and the photosensor P1 may have the same size and align almost or exactly with each other to the left and right edge, so do the pairs S2-P2, S5-P5 and S6-P6. In some embodiments, the scintillators S3 and S4 near the chips 710-A and 710-B may have a bigger size than scintillator S1, S2, S5, or S6. The scintillator S3 and photosensor P3 may have different sizes and at least one edge may not be aligned, so does S4-P4 pair. The gaps 830 of each two adjacent scintillators may be identical, as shown in the FIG. 10. The centerlines of gaps 830 between each two adjacent scintillators 810 may be in accordance with the centerlines of gaps 740 between each two adjacent photosensors 720. The anti-scatter grid 820 may include grid walls G1, G2, G3, G4 and G5. The grid walls G1 to G5 of the anti-scatter grid 820 with the thickness t and the height h may be mounted on the gaps between two adjacent scintillators. It should be noted that the number, shape, size or structure of the photosensor 720, the scintillator 810 and the anti-scatter grid 820 here are merely for the purposes of describing conveniently, and is not intended to be limiting. For persons having ordinary skills in the art, the number of the scintillator elements can be varied arbitrarily according to some embodiments of the present disclosure.

In some embodiments, there may be an additional protecting region (not shown in FIG. 9) near the edges of the chips 710-A and 710-B, and/or a gap 730 between two adjacent chips. These may cause the gaps between two photosensors in the edges of two neighbor chips be bigger than the gap, i.e., the gap between photosensors P1 and P2 may be smaller than the gap between photosensors P3 and P4. The grid walls G1 to G5 of the anti-scatter grid 820 may be arranged in a manner of each grid wall on each gap. For example, the grid wall may be placed above the gap 830 between the scintillators as shown in FIG. 10. The centerline of the grid wall and the centerline of the gap between the scintillators may coincide on a line, or have an offset distance. The thickness t of the grid walls G1 to G5 may be the same or different. The height h of the grid walls G1 to G5 may be the same or different. The width w of primary radiation region between each two adjacent grid walls may be the same or different. In some embodiments, the thickness t and the height h of the grid walls and the width w of primary radiation region may be set according to some rules. For illustration purposes, the rule may be the scatter-to-primary ratio (SPR). In some embodiments, the SPR value may be calculated by the equation SPR=S/P, wherein P is the intensity of the primary radiation and S is the intensity of the scatter radiation.

Figure 11:
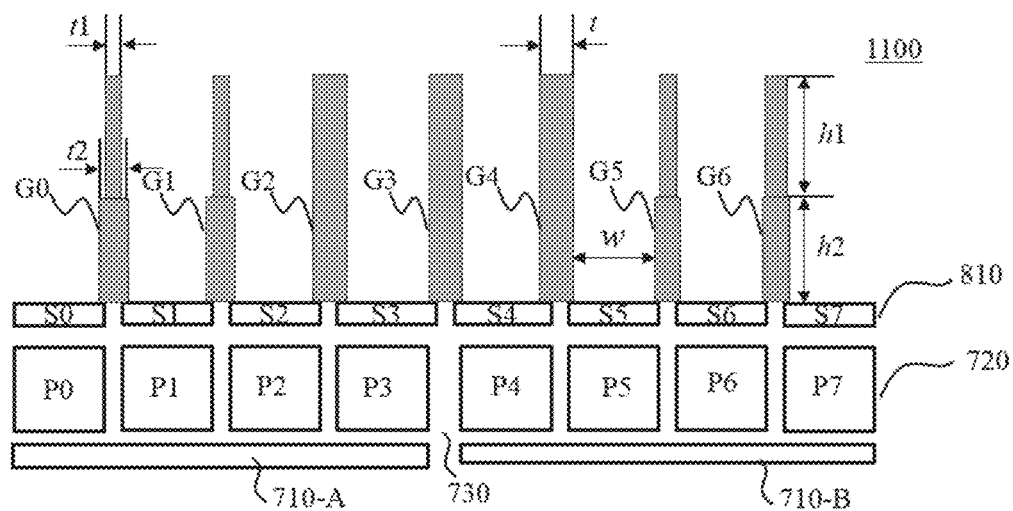

Those skilled in the art should understand that the above embodiments are only utilized to describe the present disclosure. There are many modifications and variations to the present disclosure without departing from the spirits of the present disclosure. For example, the size of each photosensors may be different or same in some embodiments of the present disclosure. The size of each scintillators may be different or same in some embodiments. The size of gaps between the photosensors may be different or same in some embodiments. The thickness t of each anti-scatter grid wall G may be different or same in some embodiments. The height h of the grid walls G1 to G5 may be different or same in some embodiments. The width w of the primary radiation region between two adjacent grid walls may be different or same in some embodiments. In some embodiments, the anti-scatter grid wall may be trapezoid, taper, triangle, or other shapes such as a handstand T shape (the thickness t2 at the bottom is larger than that on the top t1, as shown in FIG. 11), or any irregular shape, or the like, or the combination thereof. For another example, the chip 710 may be circular, oval, rectangular, rhombus, or the like, or any irregular shape, or any combination thereof. The chip 710 may be arranged regularly or irregularly. The number of the column and row of the chip 710 may be varied arbitrarily but not limited here. The photosensor 720 may be circular, oval, rectangular, rhombus, or the like, or any irregular shape, or any combination thereof. The photosensor 720 may be arranged regularly, or irregularly. The number of the column and row of the photosensor 720 may be varied arbitrarily but not limited here. The scintillator 810 may be circular, oval, rectangular, rhombus, or the like, or any irregular shape, or any combination thereof. The scintillator 810 may be arranged regularly or irregularly. The number of the column and row of the scintillator 810 may be varied arbitrarily but not limited here. The cross-section shape of the anti-scatter grid 820 may be circular, oval, rectangular, rhombus, or the like, or any irregular shape, or any combination thereof. The anti-scatter grid wall in one dimension may be parallel to each other, or have an angle between each other. It should be noted that the FIG. 10 is just examples for understanding the present disclosure, variations, deformations and/or modifications like those are not departing from the spirits of the present disclosure.

As illustrated in FIG. 10, there may be some factors influencing the quality of an image. The quality of an image may include an image size, an image resolution, an image contrast, an image with less artifacts, etc. The factors may include the primary radiation intensity received on each pixel of the scintillator, the scatter signal intensity absorbed by each grid wall (or received by each pixel of the scintillator) or the scatter-to-primary ratio (SPR), or other factors, or any combination. In some embodiments, the primary radiation intensity received by each pixel of the scintillator may be uniform. In some other embodiment, the scatter radiation intensity absorbed by each grid wall may be the uniform. In some other embodiments, the ratio of scatter radiation intensity to primary radiation intensity may be uniform. In some embodiments, other factors may be the uniformity of the width w of the primary radiation region or the uniformity of may scatter radiation w/t, wherein t is the thickness of each grid wall. In some embodiments, other factors may be the uniformity of the width w of the primary radiation region or the uniformity of may scatter radiation w/h, wherein h is the height of each grid wall.

For the embodiments mentioned above, the factors may be modified to realize the image quality by design a favorable parameter of the grid wall in the anti-scatter grid 820. In some embodiments, the parameter of the grid wall may include a shape, a size, a position, or the like, or any combination thereof. In some embodiments, the shape of the grid wall may include a triangle, a rectangle, a square, a trapezoid, a pentagon, a hexagon, a circular, an ovoid, an ellipse, an irregular shape, or the like, or any combination thereof. Merely by way of example, the irregular shape may be a T shape, e.g., its bottom thickness t2 may be no less than its top thickness t1 as shown in FIG. 11. In some embodiments, the size of the grid wall may include a thickness t, a height h, an aspect ratio h/t, a space w between two grid walls (i.e., the width w of the primary radiation region), a ratio w/t, or the like, or any combination. Merely by way of example, for the T shape grid wall, the parameters may further include t1/t2, h1/h2, w/h1, w/h2, iv/(h1+h2), as shown in FIG. 11. In some embodiments, as shown in FIG. 11, the bottom height h2 of the T shape grid wall may be no more than the top height h1. In some embodiments, the position of a grid wall may mean whether its centerline align with the centerline of the gap between the scintillators. In some embodiments, other parameters design a favorable anti-scatter gird may include the effective utilization rate of the pixels of the scintillators, the error of the size of the scintillators, the error existing in making the anti-scatter grid, the error lying in aligning the anti-scatter grid with the X-ray detector, or the like, or any combination thereof. For illustration purposes, FIG. 10 may be an example to describe how to determine the uniform width w of primary radiation region.

As shown in FIG. 10, the thickness t of the grid walls G1-G5 may be the same as or different from each other and the height h of the grid walls G1-G5 may be the same as or different from each other. The centerline of the grid walls G1-G5 may be aligned with or may be offset from the centerline of the gap between the scintillators. The centerline of the grid wall G3 may align with the centerline of the gap between the scintillator S3 and S4. The thickness of the G2 and G4 may be the same, which may be a little larger than the thickness of grid wall G3. The centerlines of the grid walls G2 and G4 may be offset from the centerlines of the gaps between the scintillators S2-S3 and S4-S5. The thickness of the G1 and G5 may be the same, which may be a little smaller than the thickness of grid wall G2 or G4. The centerlines of the grid walls G1 and G5 may be offset from the centerlines of the gaps between the scintillators S1-S2 and S5-S6. All the sizes or the positions of the grid walls in the anti-scatter grid 820 as shown in FIG. 10 may be used to arrive a uniform width w of any primary radiation region between two adjacent grid walls.

It should be understood that the parameters of the anti-scatter grid 820 in FIG. 10 is merely an example to illustrate the present disclosure. There are many modifications and variations to the present disclosure without departing from the spirits of the present disclosure. In some embodiments, the size and/or the position of each grid wall may be changed partly or wholly to arrive another uniform width w of primary radiation region. In some embodiments, the uniform parameter may be the ratio of primary radiation width to grid wall thickness w/t. In some embodiments, the uniform parameter may be the ratio of primary radiation width to grid wall height w/h. In some embodiments, the photosensor or scintillator in the detector may be arranged in another type as described elsewhere in the present disclosure. Variations, deformations and/or modifications like those are not departing from the spirits of the present disclosure.

FIG. 11 illustrates a longitudinal section of an X-ray detector with an anti-scatter placed on it according to some embodiments in the present disclosure. As illustrated in the figure, the detector 1100 may include a scintillator 810, a photosensor 720 and a chip 710. The scintillator 810 may be placed on the photosensor 720. The scintillator 810 may include scintillators S0, S1, S2, S3, S4, S5, S6 and S7. The photosensor 720 may include photosensors P0, P1, P2, P3, P4, P5, P6, and P7. In some embodiments, the scintillator S0 and photosensor P0 may have the same size and align almost or exactly with each other to the left and right edge, so do the pairs S1-P1, S2-P2, S5-P5, S6-P6 and S7-P7. In some embodiments, the scintillators S3 and S4 near the chips 710-A and 710-B may have a bigger size than scintillator S0, S1, S2, S5, S6 or S7. The scintillator S3 and photosensor P3 may have different sizes and at least one edge may not be aligned, so does the pair S4-P4. The gaps 830 between each two adjacent scintillators may be identical, as shown in the FIG. 11. The centerlines of gaps 830 between each two adjacent scintillators 810 may be in accordance with the centerlines of gaps 740 between each two adjacent photosensors 720. The anti-scatter grid 820 may include grid walls G0, G1, G2, G3, G4, G5 and G6. The grid walls G1 to G5 of the anti-scatter grid 820 with the thickness t may be mounted on the gaps between two adjacent scintillators. It should be noted that the number, shape, size or structure of the photosensor 720, the scintillator 810 and the anti-scatter grid 820 here are merely for the purposes of describing conveniently, and is not intended to be limiting. For persons having ordinary skills in the art, the number of the scintillator elements can be varied arbitrarily according to some embodiments of the present disclosure.

In some embodiments, there may be an additional protecting region (not shown in FIG. 11) near the edges of the chips 710-A and 710-B, and/or a gap 730 between two adjacent chips. These may cause the gaps between two photosensors in the edges of two neighbor chips be bigger than the gap, i.e., the gap between photosensors P1 and P2 may be smaller than the gap between photosensors P3 and P4. The grid walls G0 to G6 of the anti-scatter grid 820 may be arranged in a manner of each grid wall on each gap. For example, the grid wall may be placed above the gap 830 between the scintillators as shown in FIG. 11. The centerline of the grid wall and the centerline of the gap of the scintillator S1 and S2 may coincide on a line, or have an offset distance. The thickness t of the grid walls G0 to G6 may be the same or different. The height h of the grid walls G0 to G6 may be the same or different. The width w of primary radiation region between each two adjacent grid walls may be the same or different. In some embodiments, the thickness t and the height h of the grid walls and the width w of primary radiation region may be set according to some rules. For illustration purposes, the rule may be the scatter-to-primary ratio (SPR). In some embodiments, the SPR value may be calculated by the equation SPR=S/P, wherein P is the intensity of the primary radiation and S is the intensity of the scatter radiation.

For illustration purposes, FIG. 11 may be an example to describe a structure of the anti-scatter grid. As shown in the figure, the thickness t of the grid walls G0-G6 may be the same as or different from each other. The height h of the grid walls may be the same as or different from each other. The centerline of the grid walls G0-G6 may be aligned with or may be offset from the centerline of the gap between the scintillators. The centerline of the grid wall G3 may align with the centerline of the gap between the scintillator S3 and S4. The thickness of the G2 and G4 may be the same, which may be a little larger than the thickness of grid wall G3. The centerlines of the grid walls G2 and G4 may be offset from the centerlines of the gaps between the scintillators S2-S3 and S4-S5. The thickness of the G1 and G5 may be the same, which may be a little smaller than the thickness of grid wall G2 or G4. The centerlines of the grid walls G1 and G5 may be offset from the centerlines of the gaps between the scintillators S1-S2 and S5-S6. All the sizes or the positions of the grid walls in the anti-scatter grid 820 as shown in FIG. 11 may be used to arrive a uniform width w of any primary radiation region between two adjacent grid walls.

In some embodiments, the shape of each grid wall may be the same as or different from each other. For example, the grid walls such as G2, G3 and G4 may be rectangle, some others such as G1, G2, G6 and G7 may be T shape (the thickness h2 at the bottom is larger than the thickness h1 on the top). The rectangular grid walls such as G3, G4, and G5 may be near the edge of the gap 730 between two adjacent chips such as 710-A and 710-B. The T shaped grid walls such as G1, G2, G6 and G7 may be away from the edge of the gap 730 between two adjacent chips such as 710-A and 710-B. In some embodiments, the rectangular grid walls and the T shaped ones may be distributed alternately on the whole X-ray detector array 1100. It should be noted that FIG. 11 is merely an example for illustration. In some other embodiments, the amount and the array of the T shape grid walls may be determined by different kinds of rules. In still another embodiments, the thickness ratio t1/t2 or the height ratio h1/h2 may be variable according to specific scenarios.

Those skilled in the art should understand that the above embodiments are only utilized to describe the present disclosure. There are many modifications and variations to the present disclosure without departing from the spirits of the present disclosure. For example, the number of chip elements of each detector, the number of photosensors, scintillators, and anti-scatter grid walls on each chip element may be varied according to different demands, e.g., image resolution, the whole size of the detector and pixel, cost, or the like, or any combination thereof. For another example, the shapes of the anti-scatter grid walls may be circular, oval, rectangular, rhombus, or the like, or any irregular shape, or any combination thereof. The anti-scatter grid walls may be distributed continuously or alternately, or other ways of distribution. For still another example, the number of the different shaped grid walls in the alternative distribution may be varied arbitrarily but not limited here. In some embodiments, the uniform parameter may be the ratio of primary radiation width and grid wall height w/h. Variations, deformations and/or modifications like this are not departing from the spirits of the present disclosure.

Figure 12:
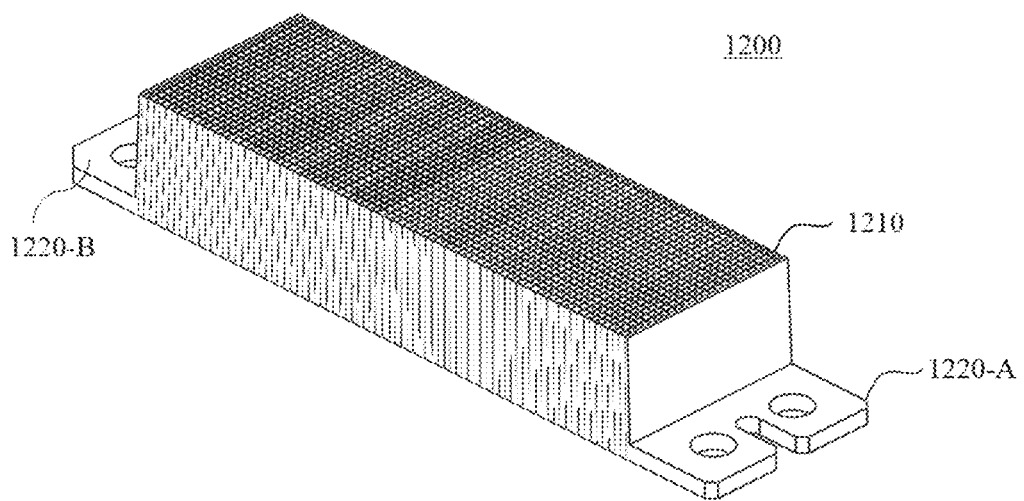
FIGS. 12-13 illustrate exemplary stereoscopic anti-scatter grids according to some embodiments of the present disclosure.

FIG. 12 shows a 3D view of an anti-scatter grid component according to some embodiments of the present disclosure. As shown in this figure, the anti-scatter grid component may include an anti-scatter grid 1210 and one or more cantilevers 1220. The anti-scatter grid 1210 may include a plurality of grid walls and grid cells which may be referred as the interspace between the grid walls. The anti-scatter grid 1210 may be configured to absorb and/or block the scatter radiation from the subject under examination or other radiation source, and at the same time more direct radiation from the X-ray generating unit may be detected by an X-ray detector. The cantilevers 1220 may include a hole thereon which may be configured or used to fix the anti-scatter grid with an X-ray detector through the holes on them.

It should be noted that the case showed in FIG. 12 is merely an example, and should not be understood as the only embodiments. There are many modifications and variations to the present disclosure without departing from the spirits of the present disclosure below.

In some embodiments, the shape of the anti-scatter grid may be flat, arc-shaped, circular, or the like, or any combination thereof. The grid walls of the anti-scatter grid may be parallel or focused. The grid walls of the anti-scatter grid may be perpendicular to or be angled with the bottom of the anti-scatter grid. The bottom surface area of the grid wall may be the same as or greater than the top surface area of the grid wall. In some embodiments, the thickness of the grid walls may be the same or different, regular or irregular. In some embodiments, the shape of the grid walls in the longitudinal section may be a triangle, a rectangle, a square, a trapezoid, a T shape, or the like, or any combination thereof. For the T shape grid walls, as shown in FIG. 11, the length of the upper part to that of the lower part ratio may be an adjustable value according to many factors, e.g., the distance between the radiation generating unit and the detecting unit, the location error existing when scanning, the image quality, or the like, or any combination thereof.

In some embodiments, the shape of the grid cells in the cross section may be a triangle, a rectangle, a square, a trapezoid, a pentagon, a hexagon, a circular, an ovoid, an ellipse, an irregular shape, or the like, or any combination thereof.

In some embodiments, the grid walls may be made from some absorbing materials including lead, gold, tungsten, depleted uranium, thorium, barium sulfate, tantalum, iridium, osmium, or the like, or any combination thereof. For the T shape grid walls, the material of the upper part of the grid walls may be the same as or different from that of the lower part. The grid cells may be made from some material with lower absorbability than that of the grid walls, e.g., metal, inorganic materials, organic materials, or the like, or any combination thereof.

The cantilever 1220 may be configured or used to fix the anti-scatter grid with an X-ray detector through the holes on them. In some embodiments, as shown in FIG. 12, the cantilevers 1220 may be a portion of the anti-scatter grid 1210 by using some manufacturing process including cutting, casting, welding, lithographic micromachining, stacking, 3D printing, or the like, or any combination thereof. In some embodiments, they may be independent and be connected by some method. The connection may be may be detachable, non-detachable, or the combination thereof. The detachable manner may be a magnetic connection, a threaded connection, a pin connection, a hinged connection or be other ways of plugging, interlocking, or the like, or any combination thereof. The non-detachable manner may be the way of welding, riveting, casting, gluing, or the like, or any combination thereof. As shown in FIG. 12, there may be two cantilevers set on both sides of the anti-scatter grids symmetrically, 1220-A and 1220-B. It should be noted that the number of and the position of the cantilevers are merely provided for the purposes of describing conveniently, and is not intended to be limiting. For persons having ordinary skills in the art, the number of and the position of the cantilevers can be varied or modified. For example, the cantilevers may be set on each side of the anti-scatter grid, and the locations of the cantilevers may be symmetrical or asymmetrical. And in some embodiments, there may be a whole cantilever surrounding the anti-scatter grid.

In some embodiments, the cantilevers may be made from some materials which may be metallic or nonmetallic, magnetic or nonmagnetic. In some embodiments, the metallic materials may include iron, copper, aluminum, tin, nickel, gold, silver, lead, zinc, or the like, alloy, or the like, or the combination thereof. In some embodiments, the nonmetallic materials may be plastic, rubber, wood, or the like, or the combination thereof.

Figure 13:
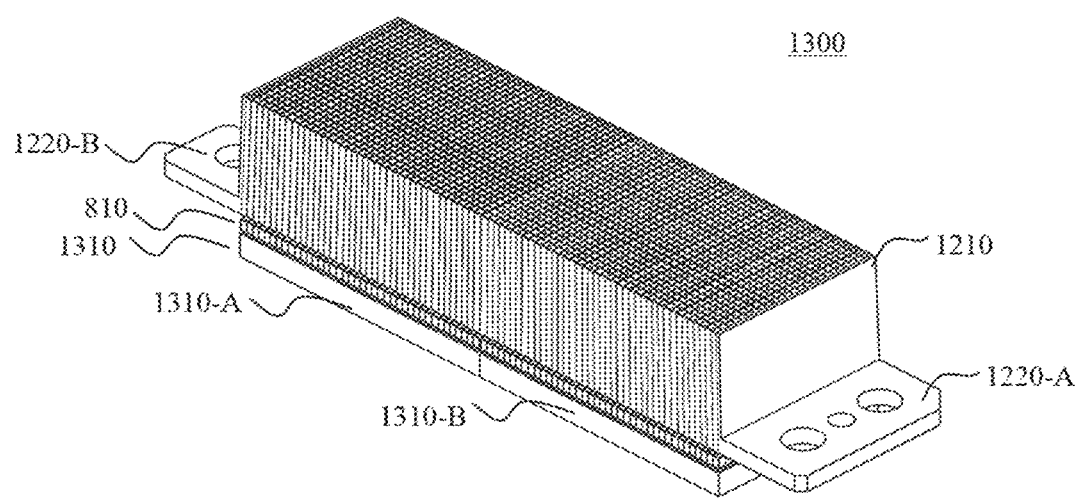

FIG. 13 shows a 3D view of an X-ray detector with an anti-scatter grid component 1200 mounted on according to some embodiments of the present disclosure. The X-ray detector 1300 may include a scintillator array 810, a photosensor array and a substrate, wherein the scintillator array and the photosensor array may be integrated together and represented by the number 1310 in this figure. In some embodiments, the photosensor may include a part 1310-A and a part 1310-B. The part 1310-A and 1310-B may positioned on different substrates. Through the cantilevers on the anti-scatter grid 1210, the X-ray detector and the anti-scatter grid 1210 may be fixed on a gantry. In some embodiments, the X-ray detector may be set on the gantry firstly and then the anti-scatter may be added on it. In some embodiments, the anti-scatter grid may be mounted on the detector then the integrated device may be fixed on the gantry. The connection may be detachable, non-detachable, or the combination thereof. The detachable manner may be a magnetic connection, a threaded connection, a pin connection, a hinged connection or be other ways of plugging, interlocking, or the like, or any combination thereof. The non-detachable manner may be the way of welding, riveting, casting, gluing, or the like, or any combination thereof.

It should be understood that the parameters of the anti-scatter grid 820 in FIG. 13 is merely an example to illustrate the present disclosure. There are many modifications and variations to the present disclosure without departing from the spirits of the present disclosure. In some embodiments, the size and/or the position of each grid wall may be changed partly or wholly to arrive another uniform width w of primary radiation region. In some embodiments, the uniform parameter may be the ratio of primary radiation width and grid wall thickness w/t. In some embodiments, the photosensor or scintillator in the detector may be arranged in another type as described elsewhere in the present disclosure. Variations, deformations and/or modifications like those are not departing from the spirits of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirits and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

What is claimed is:

1. An anti-scatter grid located on a detector comprising a plurality of chips and a plurality of photosensors assembled on each of the plurality of chips, a chip of the plurality of chips being configured to process data from the plurality of photosensors, the anti-scatter grid comprising:
a plurality of grid walls,
wherein the plurality of grid walls include:
first grid walls, each first grid wall located directly above a chip of the plurality of chips; and
second grid walls, each second grid wall located directly above a gap between two adjacent chips of the plurality of chips,
wherein a thickness of the first grid wall is different from a thickness of the second grid wall, thereby making an interspace between two adjacent grid walls uniform.

2. The anti-scatter grid of claim 1, a ratio of the width of the interspace between two adjacent grid walls of the plurality of grid walls to the height of the two adjacent grid walls of the plurality of grid walls being uniform.

3. The anti-scatter grid of claim 1, the shape of the grid wall of the plurality of the grid walls comprising a rectangle, a trapezoid, a T shape, or an irregular shape in a longitudinal section.

4. The anti-scatter grid of claim 3, at least one of the plurality of the grid walls having a shape of a rectangle, and at least one of the plurality of the grid walls having a T shape.

5. The anti-scatter grid of claim 3, the grid wall of T shape comprising a first part and a second part, the first part having a first thickness and a first height, and the second part having a second thickness and a second height, the first thickness being no less than the second thickness, and the first height being no more than the second height.

6. The anti-scatter grid of claim 1, the anti-scatter grid being a parallel one or a focused one.

7. A detector comprising:
a plurality of chips;
a plurality of photosensors assembled on each of the plurality of chips, the chip being configured to process data from the photosensor;
a plurality of scintillators, each scintillator of the plurality of scintillators being assembled on a photosensor of the plurality of photosensors; and
an anti-scatter grid located on the plurality of scintillators, the anti-scatter grid comprising a plurality of grid walls,
wherein the plurality of grid walls include:
a first grid wall located directly above a first gap between two adjacent photosensors assembled on a same chip of the plurality of chips; and
a second grid wall located directly above a second gap between two adjacent photosensors assembled on different chips of the plurality of chips,
wherein a thickness of the first grid wall is different from a thickness of the second grid wall, thereby making an interspace between two adjacent grid walls of the plurality of grid walls uniform.

8. The detector of claim 7, the chip being covered by the photosensor, the photosensor being covered by the scintillator, and the scintillator being covered by the anti-scatter grid.

9. The detector of claim 7, the plurality of photosensors having a same size and being arranged in a regular way.

10. The detector of claim 7, the scintillator in the chip having the same size with its corresponding photosensor and aligning to the left and right simultaneously with its corresponding photosensor.

11. The detector of claim 7, a grid wall of the plurality of the grid walls having at least one parameter selected from thickness, height, shape, or position of the grid wall, or width of an interspace between two adjacent grid walls of the plurality of grid walls.

12. The detector of claim 11, each grid wall of the plurality of grid walls being located at a gap between two adjacent scintillators.

13. The detector of claim 11, the centerline of a grid wall of the plurality of grid walls being offset from the centerline of the gap between two adjacent scintillators.

14. The detector of claim 11, the thickness of the grid wall of the plurality of grid walls being no less than the gap between two adjacent scintillators.

15. The detector of claim 7, a ratio of a width of an interspace between two adjacent grid walls of the plurality of grid walls to a height of the two adjacent grid walls of the plurality of grid walls being uniform.

16. The detector of claim 7, the anti-scatter grid being a parallel one or a focused one.

17. A radiation imaging system comprising:
a generator configured to generate a radiation;
a detector configured to detect the radiation; and
a processor configured to process a radiation image,
wherein the detector is as claimed in claim 7.

18. The detector of claim 7, wherein the plurality of scintillators includes a first scintillator and a second scintillator,
the first scintillator having the same size with its corresponding photosensor and aligning to the left and right simultaneously with its corresponding photosensor,
the second scintillator having different size with its corresponding photosensor and at least one edge being not aligned with its corresponding photosensor.

19. The detector of claim 18, wherein the second scintillator has a bigger size than the second scintillator.

* * * * *